United States Patent
Tang et al.

(10) Patent No.: US 10,566,291 B2
(45) Date of Patent: Feb. 18, 2020

(54) MARK STRUCTURE FOR ALIGNING LAYERS OF INTEGRATED CIRCUIT STRUCTURE AND METHODS OF FORMING SAME

(71) Applicant: GLOBALFOUNDRIES INC., Grand Cayman (KY)

(72) Inventors: Ming Hao Tang, Ballston Lake, NY (US); Yuping Ren, Clifton Park, NY (US); Rui Chen, Clifton Park, NY (US); Bradley Morgenfeld, Greenfield Center, NY (US); Zheng G. Chen, Poughkeepsie, NY (US)

(73) Assignee: GLOBALFOUNDRIES INC., Grand Cayman (KY)

( * ) Notice: Subject to any disclaimer, the term of this patent is extended or adjusted under 35 U.S.C. 154(b) by 0 days.

(21) Appl. No.: 15/898,606

(22) Filed: Feb. 18, 2018

(65) Prior Publication Data
US 2019/0259708 A1    Aug. 22, 2019

(51) Int. Cl.
| | |
|---|---|
| *H01L 23/544* | (2006.01) |
| *G03F 9/00* | (2006.01) |
| *G03F 7/20* | (2006.01) |
| *G01N 21/95* | (2006.01) |
| *H01L 21/66* | (2006.01) |

(52) U.S. Cl.
CPC ....... *H01L 23/544* (2013.01); *G01N 21/9501* (2013.01); *G03F 7/70466* (2013.01); *G03F 7/70633* (2013.01); *G03F 9/7076* (2013.01); *G03F 9/7084* (2013.01); *H01L 22/12* (2013.01)

(58) Field of Classification Search
CPC combination set(s) only.
See application file for complete search history.

(56) References Cited

U.S. PATENT DOCUMENTS

| | | | |
|---|---|---|---|
| 8,455,982 B2 | 6/2013 | Chen et al. | |
| 9,129,974 B2 | 9/2015 | Hsieh et al. | |
| 2002/0142235 A1* | 10/2002 | Hamanaka | G03F 9/7076 430/5 |
| 2004/0051127 A1* | 3/2004 | Tanaka | H01L 23/544 257/296 |
| 2006/0088990 A1* | 4/2006 | Menon | H01L 21/76895 438/597 |
| 2006/0103035 A1* | 5/2006 | Maruyama | H01J 37/3045 257/797 |
| 2006/0117293 A1 | 6/2006 | Smith et al. | |

(Continued)

OTHER PUBLICATIONS

Related TW Patent Application No. 108101664, Office Action dated Oct. 28, 2019, 7 pages.

*Primary Examiner* — Cuong B Nguyen
(74) *Attorney, Agent, or Firm* — Anthony Canale; Hoffman Warnick LLC

(57) ABSTRACT

This disclosure relates to a structure for aligning layers of an integrated circuit (IC) structure that may include a first dielectric layer positioned above a semiconductor substrate having one or more active devices, a trench stop layer positioned above the first dielectric layer, a second dielectric layer positioned above the trench stop layer, and a plurality of metal-filled marking trenches extending vertically through the second dielectric layer and the trench stop layer and at least partially into the first dielectric layer. The metal-filled trenches are electrically isolated from any active devices contained in the IC.

19 Claims, 15 Drawing Sheets

(56) References Cited

U.S. PATENT DOCUMENTS

| | | | |
|---|---|---|---|
| 2008/0157384 A1* | 7/2008 | Jeon | G03F 9/7076 257/770 |
| 2009/0134496 A1* | 5/2009 | Warrick | G03F 9/7076 257/620 |
| 2013/0084655 A1 | 4/2013 | Yue et al. | |
| 2015/0200165 A1 | 7/2015 | Shiba et al. | |
| 2016/0351573 A1 | 12/2016 | Yoshino et al. | |
| 2017/0294342 A1 | 10/2017 | Lu et al. | |

* cited by examiner

MARK STRUCTURE FOR ALIGNING LAYERS OF INTEGRATED CIRCUIT STRUCTURE AND METHODS OF FORMING SAME

BACKGROUND

Technical Field

The present disclosure relates to structures formed in an integrated circuit (IC) structure to align multiple vertical layers with each other, particularly in IC structures formed with multiple patterning techniques. More particularly, the present disclosure relates to a mark structure for aligning layers of an integrated circuit (IC) structure, and methods of forming the same.

Related Art

Integrated circuit fabrication requires forming large numbers of interconnected devices, such as transistors, resistors, capacitors, and diodes on the surface of a semiconductor substrate material. These devices are formed in part by selectively depositing and removing multiple layers of material, e.g., semiconductors, insulators, photoresists, masks, etch stop layers, and metals. The functionality and reliability of a particular IC depends at least partially on accurate vertical alignment between each of the layers. In some cases, a fabricator may use multiple patterning lithography to place some elements in closer lateral proximity with each other than may otherwise be possible through conventional manufacturing techniques.

Double patterning lithography is one type of multiple patterning lithography technology that has been in use for some time. Double patterning lithography generally involves creating shapes, e.g., one or more conductive elements for providing functional features and/or electrical connections within a device, that are within the same design layer but too close to each other to be assigned to the same mask layer. The shapes are instead assigned onto two different mask layers in order to satisfy spacing requirements specified in the design of the product. These two different mask layers are then used to create one layer of the IC. Other multiple patterning lithography options such as triple patterning lithography may use more than two masks. Accurate alignment between the multiple mask layers is therefore one of several important factors in fabrication of functional and reliable ICs.

Accurate alignment between mask layers may be accomplished by several approaches. One of these approaches includes forming one or more marking structures, such as one or more overlay marks and/or one or more alignment marks in various layers of the IC as it is being processed. During lithography, i.e., the printing of each layer in an IC structure, a fabricator may detect the location of a marking structure in each layer to determine whether multiple layers are aligned with each other. In the event that the detected marking structure in previously-formed layer is not in its anticipated position, the fabricator may adjust the relative position of the partially fabricated IC and the current mask reticle to bring the prior mask layer and the current mask reticle into proper alignment with one another before printing the next layer. In addition, following the lithography process, marking structures may be measured by a stand-alone or in-situ metrology tool to quantify the alignment of the current layer, imaged in photoresist, relative to the prior layer etched into the substrate, to detect if misaligned features are present. This overlay mark metrology data then allows a determination to be made to continue fabrication, conduct rework operations and feedback offsets, or discard a defective IC.

Typical marking structures may include several linear metal-filled trenches arranged parallel to one another within a dielectric material. The trenches may be arranged in groups where trenches within a group are in close proximity to one another, and multiple groups are arranged to form a structure for use as an overlay mark or alignment mark. The metal in these trenches is electrically isolated from the various devices, such as transistors, and may not have any function in the finished IC. Marking structures may optionally be positioned in kerf lines between individual dies on the semiconductor substrate. The effectiveness of a marking structure is at least partially dependent on the contrast between the materials and the background material of the partially fabricated IC. Higher contrast can improve the accuracy of imaging of the marking structure and thus the accuracy of final alignment between the various layers in an IC.

Conventional methods of forming marking structures may produce marking trenches with a metal fill that is not thick enough to produce good contrast against the background when imaged. Conventional methods may also produce marking trenches that lack uniformity. Weak contrast or non-uniformity can cause unreliable results when measuring alignment, resulting in defective product or leading to expensive and time-consuming re-work operations.

SUMMARY

A first aspect of this disclosure is directed to a structure for alignment of an integrated circuit (IC) structure, the structure including: a first dielectric layer positioned above a semiconductor substrate, the semiconductor substrate having one or more active devices thereon; a trench stop layer positioned above the first dielectric layer; a second dielectric layer positioned above the trench stop layer; and a plurality of metal-filled marking trenches extending vertically through the second dielectric layer and the trench stop layer, and at least partially into the first dielectric layer, wherein each of the plurality of metal-filled marking trenches includes a metal electrically isolated from the one or more active devices by at least the first dielectric layer.

A second aspect of this disclosure is directed to a method of forming a structure for alignment of an integrated circuit (IC) structure, the method including: forming a via hard mask on a precursor structure, wherein the precursor structure includes a semiconductor substrate, a first dielectric layer positioned above the semiconductor substrate, a trench stop layer positioned above the first dielectric layer, a second dielectric layer positioned above the trench stop layer, a first hard mask positioned above the second dielectric layer and including a plurality of preformed openings therein, a plurality of substantially parallel trench spacers positioned above the first hard mask between the plurality of preformed openings, a spin-on hard mask positioned over and between the plurality of trench spacers, and a via stop layer positioned above the spin-on hard mask; forming a plurality of first openings within the via hard mask wherein the plurality of first openings are either substantially perpendicular to the plurality of trench spacers or substantially parallel to the plurality of trench spacers, and wherein the plurality of first openings are positioned above the plurality of trench spacers; expanding the plurality of first openings within the via hard mask by removing a plurality of strips of the via hard mask, wherein the plurality of strips are either substantially perpendicular to the plurality of trench spacers or substantially parallel to the plurality of trench spacers, and wherein the plurality of strips are positioned between pairs of the plurality of first openings such that substantially all of the via hard mask positioned above the plurality of trench spacers is removed to make an expanded opening; removing a portion of the via stop layer, a portion of the spin-on hard mask, and a portion of the second dielectric layer positioned underneath the plurality of preformed openings within the first hard mask; removing a portion of the trench stop layer and a portion of the first dielectric layer positioned underneath the expanded opening and positioned between the plurality of trench spacers to form a plurality of marking trenches; and forming a metal within at least one of the plurality of marking trenches.

A third aspect of this disclosure is directed to a method of forming a structure for alignment of an integrated circuit (IC) structure, the method including: forming a via hard mask on a precursor structure, wherein the precursor structure includes a semiconductor substrate, a first dielectric layer positioned above the semiconductor substrate, a trench stop layer positioned above the first dielectric layer, a second dielectric layer positioned above the trench stop layer, a first hard mask positioned above the second dielectric layer, a spin-on hard mask positioned above the first hard mask, and a via stop layer positioned above the spin-on hard mask, wherein the first hard mask has a plurality of preformed openings through the first hard mask; forming a plurality of first openings within the via hard mask wherein the plurality of first openings are either substantially perpendicular to the plurality of preformed openings through the first hard mask or substantially parallel to the plurality of preformed openings through the first hard mask, and wherein the plurality of first openings are positioned above the plurality of preformed openings through the first hard mask; expanding the plurality of first openings within the via hard mask by removing a plurality of strips of the via hard mask, wherein the plurality of strips are either substantially perpendicular to the plurality of preformed openings through the first hard mask or substantially parallel to the plurality of preformed openings through the first hard mask, and wherein the plurality of strips are positioned between pairs of the plurality of first openings such that substantially all of the via hard mask positioned above the plurality of preformed openings through the first hard mask is removed to make an expanded opening; removing a portion of the via stop layer, a portion of the spin-on hard mask, and a portion of the second dielectric layer positioned underneath the expanded opening; removing a portion of the trench stop layer and a portion of the first dielectric layer positioned underneath the expanded opening and positioned underneath the plurality of preformed openings through the first hard mask to form a plurality of marking trenches; and forming a metal within at least one of the plurality of marking trenches.

The foregoing and other features of this disclosure will be apparent from the following more particular description of embodiments of this disclosure.

BRIEF DESCRIPTION OF THE DRAWINGS

The embodiments of this disclosure will be described in detail, with reference to the following figures, wherein like designations denote like elements.

Figure 1:
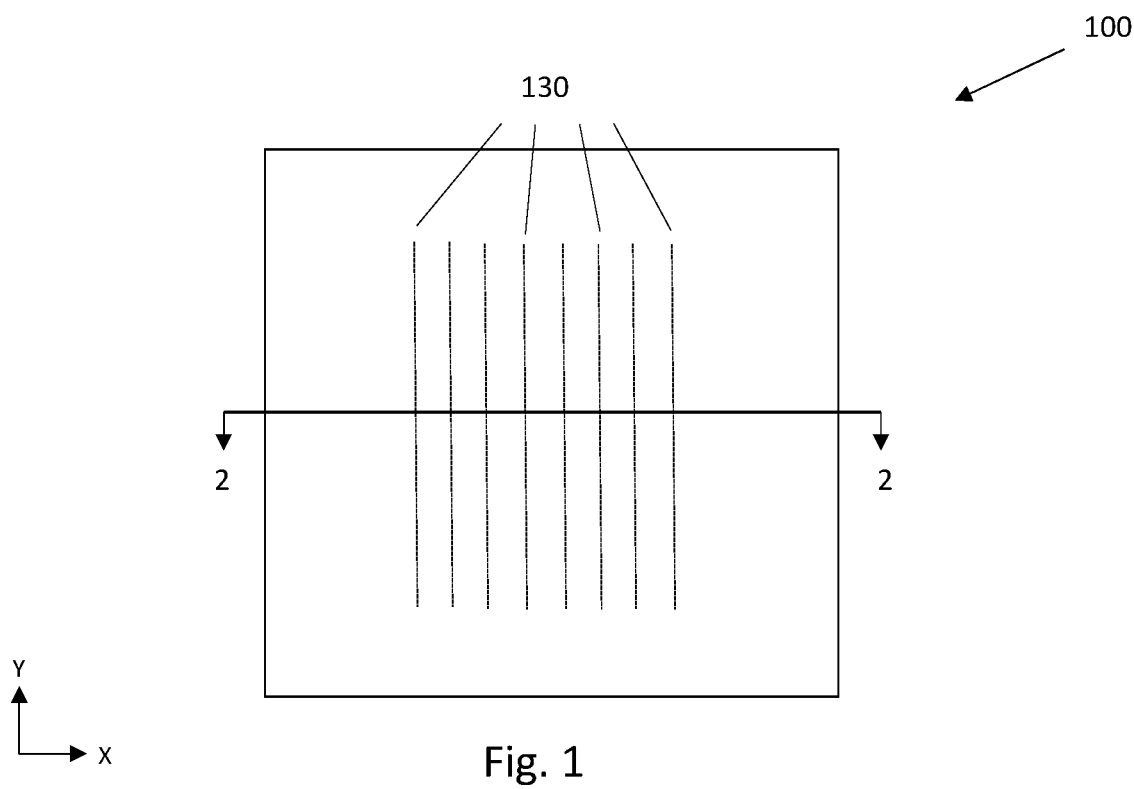
FIG. 1 shows a plan view of a precursor structure of an integrated circuit (IC) to be processed according to embodiments of this disclosure.

It is noted that the drawings of this disclosure are not to scale. The drawings are intended to depict only typical aspects of this disclosure, and therefore should not be considered as limiting the scope of this disclosure. In the drawings, like numbering represents like elements between the drawings. In certain drawings, repeated reference numbers for repeated elements are omitted for clarity.

DETAILED DESCRIPTION

Unless otherwise noted, or as may be evident from the context of their usage, any terms, abbreviations, acronyms or scientific symbols and notations used herein are to be given their ordinary meaning in the technical discipline to which the disclosure most nearly pertains. Some of the terms set forth below may be registered trademarks (®).

This disclosure relates to integrated circuit (IC) structures and fabrication techniques. More particularly, the present disclosure relates to alignment structures, alternatively "structures" hereafter, which may be used as an overlay mark, alignment mark, etc., for an IC structure. Integrated circuits are manufactured employing, among other operations, multiple processing steps that selectively add or remove material in one or more layers formed on a semiconductor substrate. Certain processing steps may entail multiple addition or removal operations on the same layer. Alternatively or additionally, multiple layers may be affected by a single operation or series of operations. Fabrication of functional and reliable ICs depends at least partially on accurate alignment between each of these layers and between each of the operations performed upon the layers.

In the following description, reference is made to the accompanying drawings that form a part thereof, and in which is shown by way of illustration specific representative embodiments in which the present teachings may be practiced. These embodiments are described in sufficient detail to enable those skilled in the art to practice the present teachings and it is to be understood that other embodiments may be used and that changes may be made without departing from the scope of the present teachings. The following description is, therefore, merely illustrative.

The fabrication steps disclosed in this disclosure may be combined with fabrication steps performed for other purposes. For example, photolithography or etching steps performed according to embodiments of this disclosure may simultaneously form other structures of the IC, including but not limited to wiring, silicon through vias, or other interconnections.

Embodiments of the present disclosure include providing a precursor structure 100 of an integrated circuit (IC) to be processed according to one aspect of this disclosure. Among other things, structures and methods according to the disclosure may feature a structure for aligning various layers of an IC, in which metal is formed within deeper marking trenches as compared to conventional alignment structures. The use of deeper marking trenches with thicker metal fill may improve imaging contrast and provide greater tolerance of non-uniformity. These improvements can increase the accuracy of alignment during fabrication, increasing yield and decreasing costs.

Figure 2:
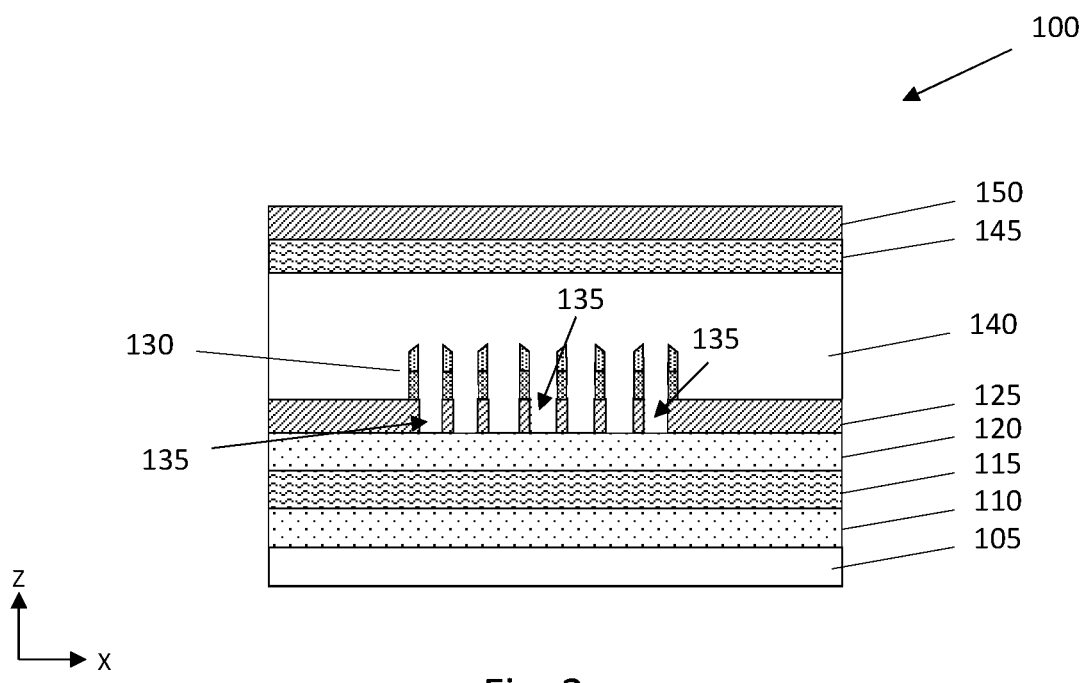
FIG. 2 shows a lateral cross section view along the line 2-2 in FIG. 1 of the precursor structure according to embodiments of this disclosure.
Figure 14:
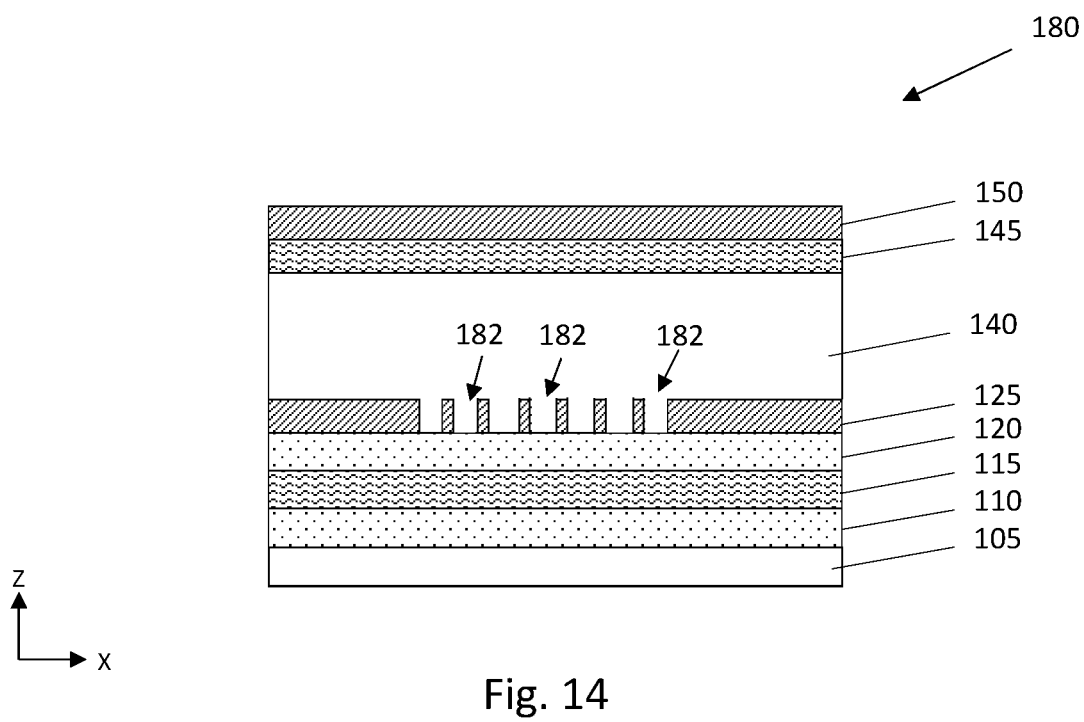
FIG. 14 shows a lateral cross section view along the line 14-14 in FIG. 13 of the precursor structure according to embodiments of this disclosure

Referring to FIGS. 1 and 2 together, FIG. 1 provides a plan view of an example precursor structure 100, while FIG. 2 provides a cross-sectional view in plane X-Z of the same structure. Embodiments of precursor structure 100 may contain one or more active devices or partially fabricated active devices (not shown, but typically on or in substrate 105) located in regions separate from the region to be used for fabrication of the marking trenches and overlay mark described in this disclosure. Precursor structure 100 may include multiple layers fabricated during previous processing steps. For example, precursor structure 100 may include a semiconductor substrate 105, a first dielectric layer 110, a trench stop layer 115, a second dielectric layer 120, a first hard mask 125, several trench spacers 130 positioned on first hard mask 125, a plurality of preformed openings 138 within first hard mask 125 and laterally between trench spacers 130, a spin-on hard-mask 140, a via stop layer 145, and a via hard mask 150. Trench spacers 130 may be positioned within spin-on hard mask 140 and adjacent to preformed openings 135 in an alternating manner on first hard mask 125. Each trench spacer 130 may include one or more currently known or later developed spacer materials suitable for integrated circuit processing, examples of which are provided herein. In some embodiments, trench spacers 130 may be omitted based on the processing techniques used to form substrate 105 and layers 110, 114, 120, 125 (e.g., as shown in FIG. 14 and discussed in further detail below). Trench spacers 130, and/or openings where applicable, may be substantially linear and extend substantially in parallel to one another. Spacing between pairs of trench spacers 130, and/or openings in alternative embodiments, may be substantially the same or may be different in different portions of precursor structure 100. Likewise, the width of trench spacers 130 may be substantially the same or may be different in different portions of precursor structure 100. The various components of precursor structure 100 are discussed herein in more detail, with reference to FIGS. 1 and 2, to aid in the description of subsequent processing and/or resulting structures.

The various components of precursor structure 100 may include a variety of materials. Substrate 105 materials may include but are not limited to silicon, germanium, silicon germanium, silicon carbide, and those consisting essentially of one or more III-V compound semiconductors having a composition defined by the formula $Al_{X1}Ga_{X2}In_{X3}As_{Y1}P_{Y2}N_{Y3}Sb_{Y4}$, where X1, X2, X3, Y1, Y2, Y3, and Y4 represent relative proportions, each greater than or equal to zero and $X1+X2+X3+Y1+Y2+Y3+Y4=1$ (1 being the total relative mole quantity). Other suitable substrates include II-VI compound semiconductors having a composition $Zn_{A1}Cd_{A2}Se_{B1}Te_{B2}$, where A1, A2, B1, and B2 are relative proportions each greater than or equal to zero and $A1+A2+B1+B2=1$ (1 being a total mole quantity). Furthermore, the entirety of substrate 105 and/or portions thereof may be strained. In some cases, semiconductor substrate 105 may take the form of a semiconductor-on-insulator (SOI) layer. An SOI layer typically refers to a layered silicon-insulator-silicon substrate in place of a more conventional silicon substrate (bulk substrate) in semiconductor manufacturing, especially microelectronics. SOI-based devices differ from conventional bulk semiconductor devices in that the semiconductor junction is above an electrical insulator, typically silicon dioxide or (less commonly) sapphire. The precise thickness of the insulating layer and topmost semiconductor layer also vary widely with the intended application.

Dielectric materials of first dielectric layer 110 and second dielectric layer 120 may include any interlevel or intralevel dielectric material including inorganic dielectric materials, organic dielectric materials, or combinations thereof. First dielectric layer 120 or second dielectric layer 120 may also include additional sublayers, such as glue layers or cap layers as known in the art. First dielectric layer 120 may be the layer known in the art as the "zero via dielectric layer." Dielectric materials may have various dielectric constants (K). High-K dielectrics, i.e., those having a dielectric constant above approximately 3.9, are employed when high capacitance is desired. Conversely, low-K and ultra-low-K dielectrics, i.e., materials having a dielectric constant of at most approximately 3.9, are employed when low capacitance is desired. Suitable dielectric materials include but are not limited to: carbon-doped silicon dioxide materials; fluorinated silicate glass (FSG); organic polymeric thermoset materials; silicon oxycarbide; SiCOH dielectrics; fluorine doped silicon oxide; spin-on glasses; silsesquioxanes, including hydrogen silsesquioxane (HSQ), methyl silsesquioxane (MSQ) and mixtures or copolymers of HSQ and MSQ; benzocyclobutene (BCB)-based polymer dielectrics, and any silicon-containing low-k dielectric. Examples of spin-on low-k films with SiCOH-type composition using silsesquioxane chemistry include HOSP™ (available from Honeywell), JSR 5109 and 5108 (available from Japan Synthetic Rubber), Zirkon™ (available from Shipley Microelectronics, a division of Rohm and Haas), and porous low-k (ELk) materials (available from Applied Materials). Examples of carbon-doped silicon dioxide materials, or organosilanes, include Black Diamond™ (available from Applied Materials) and Coral™ (available from Lam Research). An example of an HSQ material is FOx™ (available from Dow Corning).

First hard mask 125 and via hard mask 150 of precursor structure 100 each refer to a layer of material which is applied over an underlying layer of material. After processing the underlying layer, the mask may be removed. An example of a commonly used hard mask material is $Si_3N_4$ ("nitride"). Trench stop layer 115 and via stop layer 145 each refer to a layer of material which prevents damage to the underlying semiconductor or metal material during etching of layers above the stop layer. Etch stop materials feature drastically different etch characteristics than the material to be etched; a layer of etch stop material is placed underneath material to be etched to stop the etching process. Examples of commonly used stop layer materials include but are not limited to: aluminum nitride, aluminum oxide, and metal oxides of metals from groups IV, V, and VI of the periodic table, and yttrium oxide. Spin-on hard-mask 140 may be formed by one or more spin-on techniques for applying materials, which generally involves providing a stream of material to the substrate, while the substrate is spinning, resulting in a relatively thin, flat, evenly-distributed coating of the material on the underlying substrate.

Trench spacers 130 refer to etch-resistant materials which define the boundaries between adjacent trenches formed within precursor structure 100 by subsequent etching operations. Trench spacers 130 may be formed from any material known to the art, such as titanium oxide (TiO2) and/or silicon oxide ($SiO_2$). In various embodiments, the trench spacers 130 may be formed using a self-aligned double patterning (SADP) process, also known as sidewall image transfer (SIT) processing. The arrangement of trench spacers 130, or openings in alternative embodiments, will determine the arrangement of marking trenches formed during later processing steps according to embodiments of this disclosure. Trench spacers 130 in various embodiments may have a spacing in the range of between approximately 5 nanometers (nm) to approximately 100 nm.

Embodiments of precursor structure 100, and/or other precursor structures discussed herein, may be positioned laterally adjacent to one or more active devices or partially fabricated active devices (not shown, on or in substrate 105). Such devices may be located in regions separate from the region to be used for fabrication of the marking trenches and structure for use as an overlay or alignment mark described in this disclosure. Additionally or alternatively, precursor structure 100 and/or other precursor structures discussed herein may be formed in regions targeted for removal in subsequent processing steps, such as but not limited to kerf regions in an IC wafer. In various embodiments, one or more active devices may be formed in regions separate from the region to be used for fabrication of the alignment structure by subsequent processing steps.

Figure 3:
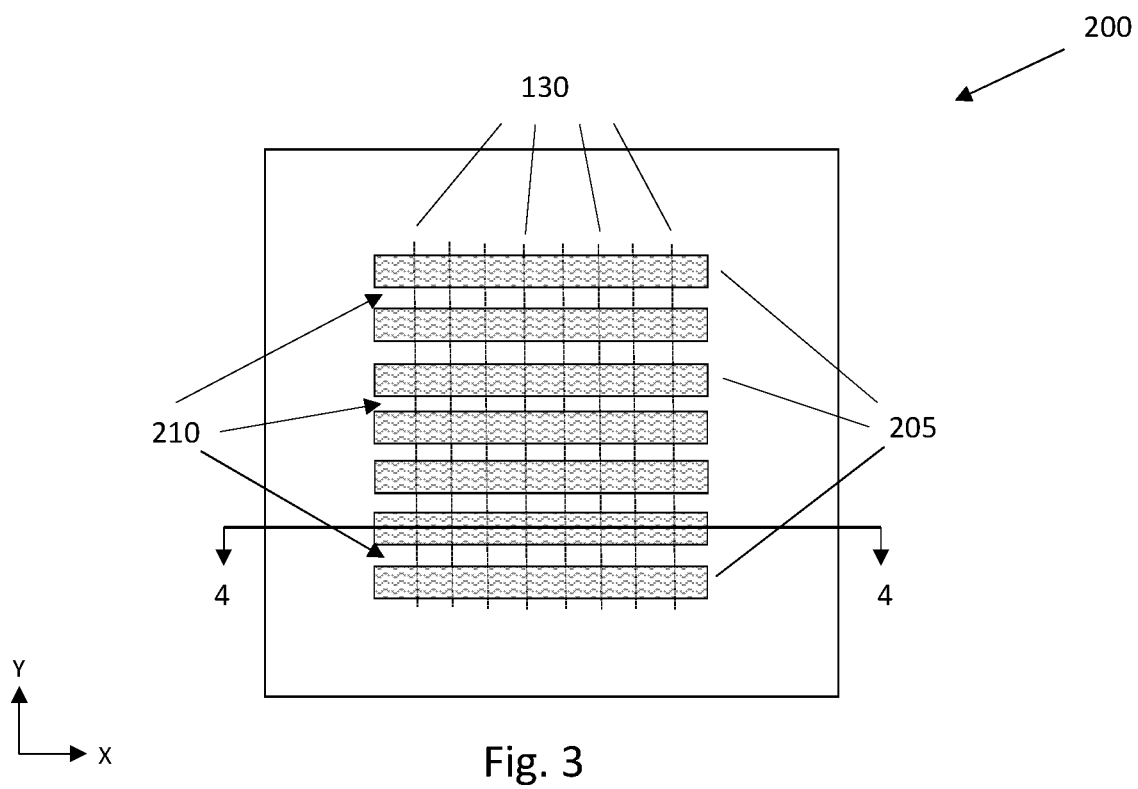
FIG. 3 shows a plan view of the IC after undergoing a first patterning operation according to embodiments of this disclosure.
Figure 4:
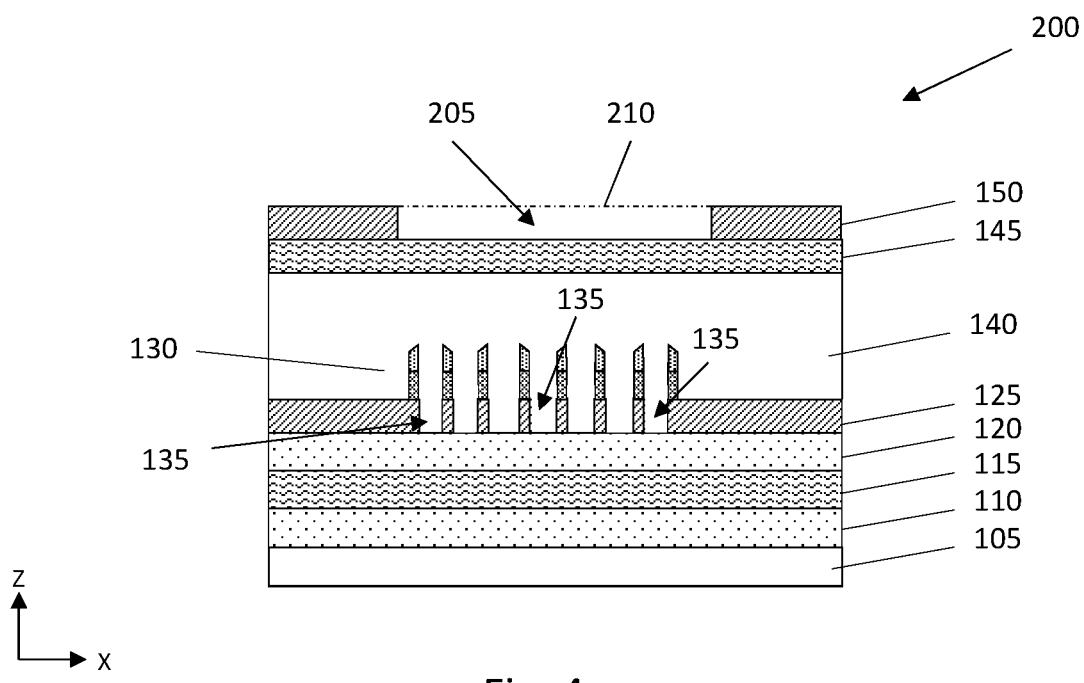
FIG. 4 shows a lateral cross section view along line 4-4 in FIG. 3 of the IC after undergoing a first patterning operation according to embodiments of this disclosure.

Turning now to FIGS. 3 and 4 together, processes for forming openings 205 in via hard mask 150 according to the disclosure are shown. FIG. 3 provides a plan view of a partially processed structure 200 with openings 205 therein, while FIG. 4 provides a cross-sectional view in plane X-Z of the same structure. Processing according to embodiments of this disclosure includes using photolithography to form multiple openings 205 through via hard mask 150 positioned above trench spacers 130. These openings may be oriented substantially perpendicular to trench spacers 130 or may be oriented substantially parallel with trench spacers 130. The width of the openings that may be reliably created by a single photolithography step is limited due to limitations of the photolithography process and due to an etch loading effect. These effects result in an unwanted via hard mask 150 residual which blocks subsequent etch processes. Therefore, the width of the openings 205 is limited to a predetermined size depending on the specific photolithography process used. Strips 210 of via hard mask material remain over trench spacers 130 after the first photolithography step above.

In lithography (or "photolithography"), a radiation sensitive "resist" coating is formed over one or more layers which are to be treated, in some manner, such as to be selectively doped and/or to have a pattern transferred thereto. The resist, which is sometimes referred to as a photoresist, is itself first patterned by exposing it to radiation, where the radiation (selectively) passes through an intervening mask or template containing the pattern. As a result, the exposed or unexposed areas of the resist coating become more or less soluble, depending on the type of photoresist used. A developer is then used to remove the more soluble areas of the resist leaving a patterned resist. The patterned resist can then serve as a mask for the underlying layers which can then be selectively treated, such as to receive dopants and/or to undergo etching, for example.

The depth of the marking trenches formed by subsequent etching processes is limited when portions of via hard mask 150 remain above trench spacers 130. Conventional methodologies that allowed residual via hard mask above the trench spacers resulted in marking trenches that penetrated only into second dielectric 120. When later filled with metal, the resulting structure may exhibit poor contrast and high variation between different regions of the IC. To address this problem, residual via hard mask material will be removed by multiple pattern lithography, including a second photolithography step according to embodiments of this disclosure, as described below. Each pattern printed in sequence is often identified in the art as being a different "color", although the significance of the colors is only to identify different patterns, and does not reflect actual colors.

Figure 5:
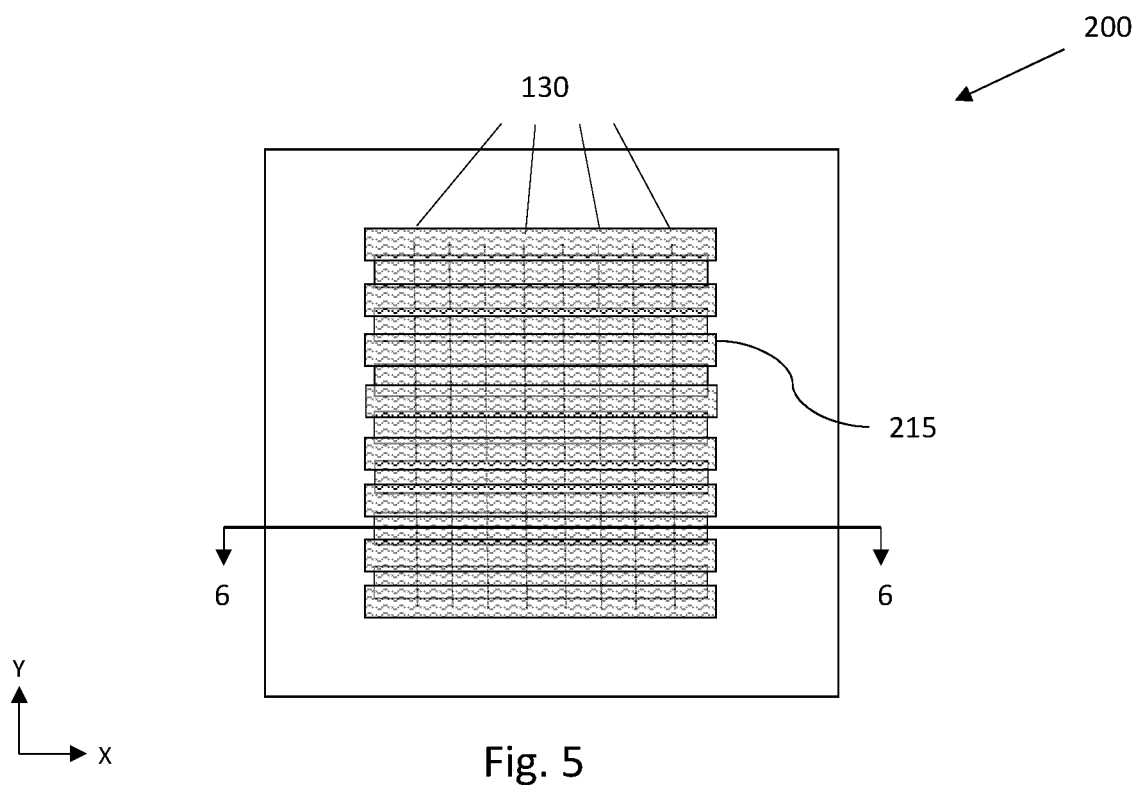
FIG. 5 shows a plan view of the IC after undergoing a second patterning operation according to embodiments of this disclosure.
Figure 6:
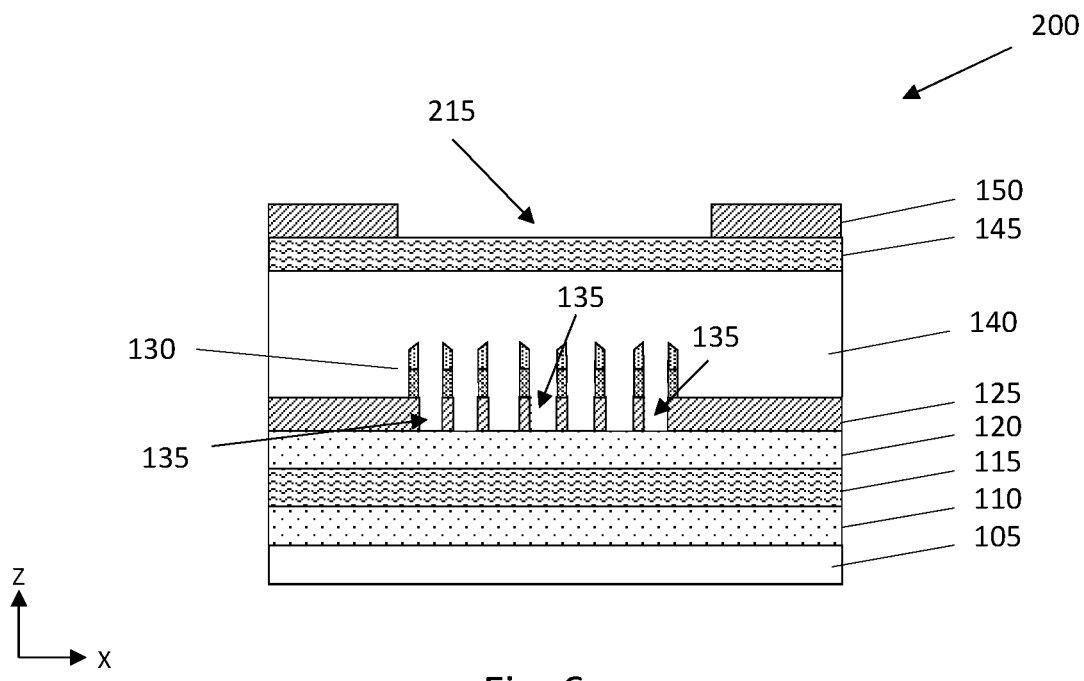
FIG. 6 shows a lateral cross section view along line 6-6 in FIG. 5 of the IC after undergoing a second patterning operation according to embodiments of this disclosure.

Proceeding to FIGS. 5 and 6 together, processes for forming expanded openings 215 in via hard mask 150 according to the disclosure are shown. FIG. 5 provides a plan view of a partially processed structure 200 with an expanded opening 215 therein, while FIG. 6 provides a cross-sectional view in plane X-Z of the same structure. Processing according to embodiments of this disclosure includes a second photolithography step, using a second "color" mask, to form an expanded opening 215 through via hard mask 150. This expanded opening 215 is positioned above trench spacers 130, by removing the strips 210 of via hard mask 150 that remained between openings 205 after the first photolithography step. The second lithography step removes substantially all of via hard mask 150 above trench spacers 130.

Figure 7:
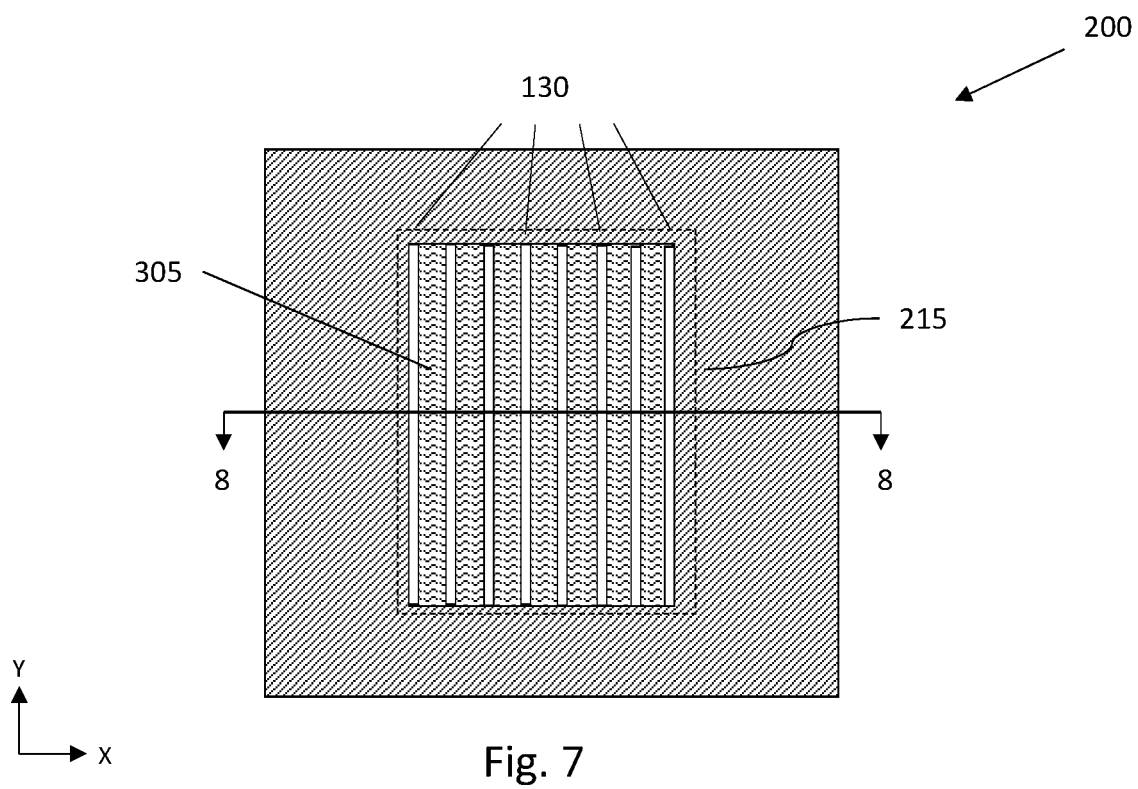
FIG. 7 shows a plan view of the IC after undergoing a first removal operation according to embodiments of this disclosure.
Figure 8:
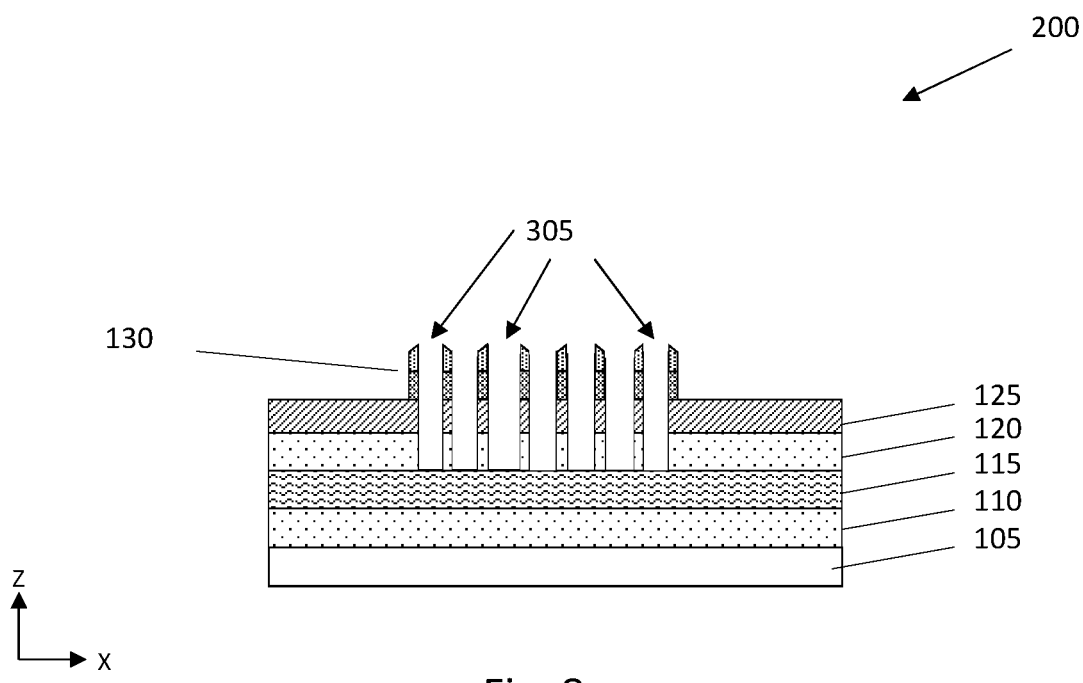
FIG. 8 shows a lateral cross section view along line 8-8 in FIG. 7 of the IC after undergoing a first removal operation according to embodiments of this disclosure.

Proceeding to FIGS. 7 and 8 together, processes for partially forming marking trenches 305 according to the disclosure are shown. FIG. 7 provides a plan view of a partially processed structure 200 with partially formed marking trenches 305 therein, while FIG. 8 provides a cross-sectional view in plane X-Z of the same structure. Processing according to embodiments of this disclosure includes removing via hard mask 150, via stop layer 145, and spin-on hard mask 140 such as by using one or more etching methods now known to the art or developed in the future. While conventional processing would typically only etch as far vertically into the IC structure as first hard mask 125, expanded opening 215 allows etching to continue to deeper layers. Portions of first hard mask 125 and second dielectric 120 may be removed underneath expanded opening 215 where not protected by trench spacers 130, forming partial marking trenches 305 between trench spacers 130.

Etching generally refers to the removal of material from a substrate (or structures formed on the substrate), and is often performed with a mask in place so that material may selectively be removed from certain areas of the substrate, while leaving the material unaffected, in other areas of the substrate. There are generally two categories of etching, (i) wet etch and (ii) dry etch. Wet etch is performed with a solvent (such as an acid) which may be chosen for its ability to selectively dissolve a given material (such as oxide), while leaving another material (such as polysilicon) relatively intact. This ability to selectively etch given materials is fundamental to many semiconductor fabrication processes. A wet etch will generally etch a homogeneous material (e.g., oxide) isotropically, but a wet etch may also etch single-crystal materials (e.g. silicon wafers) anisotropically. Dry etch may be performed using a plasma. Plasma systems can operate in several modes by adjusting the parameters of the plasma. Ordinary plasma etching produces energetic free radicals, neutrally charged, that react at the surface of the wafer. Since neutral particles attack the wafer from all angles, this process is isotropic. Ion milling, or sputter etching, bombards the wafer with energetic ions of noble gases which approach the wafer approximately from one direction, and therefore this process is highly anisotropic. Reactive-ion etching (RIE) operates under conditions intermediate between sputter and plasma etching and may be used to produce deep, narrow features, such as trenches.

Figure 9:
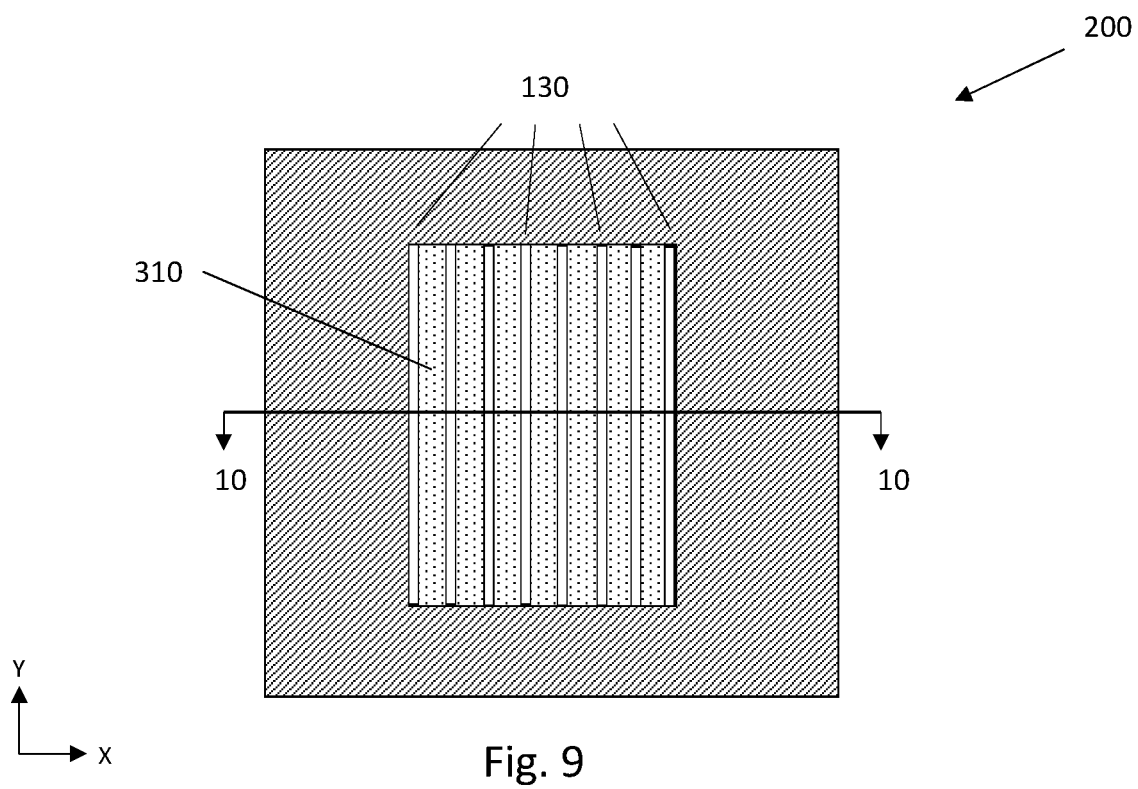
FIG. 9 shows a plan view of the IC after undergoing a second removal operation according to embodiments of this disclosure.
Figure 10:
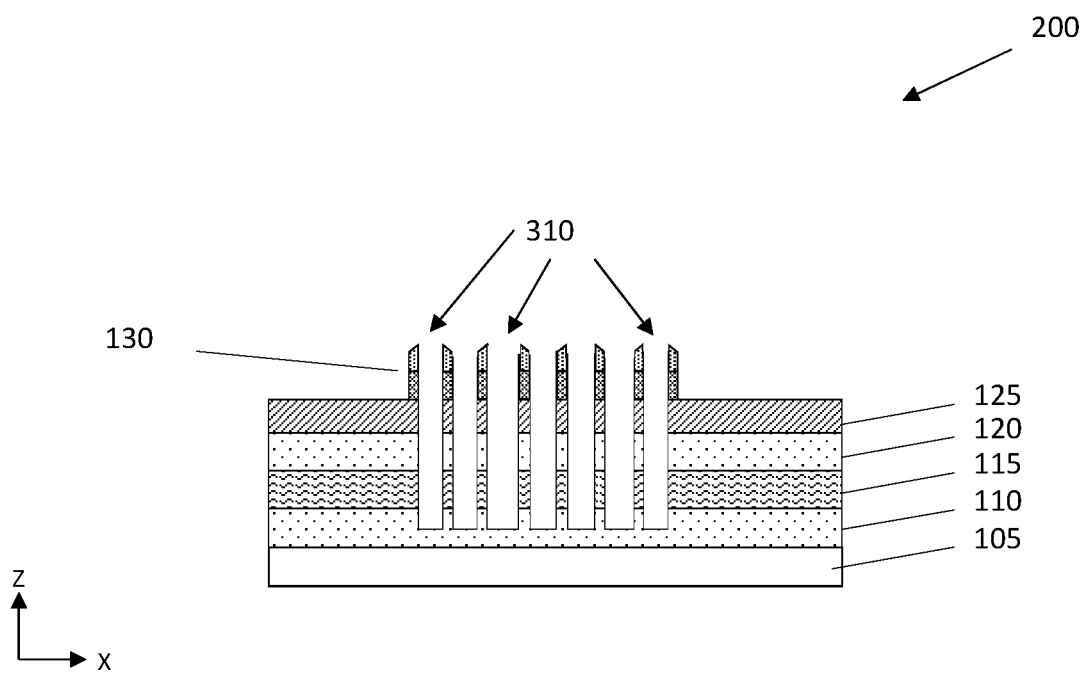
FIG. 10 shows a lateral cross section view along line 10-10 in FIG. 9 of the IC after undergoing a second removal operation according to embodiments of this disclosure.

Proceeding to FIGS. 9 and 10 together, processes for forming full-depth marking trenches 310 according to the disclosure are shown. FIG. 9 provides a plan view of a partially processed structure 200 with full-depth marking trenches 310 therein, while FIG. 10 provides a cross-sectional view in plane X-Z of the same structure. Processing according to embodiments of this disclosure includes removing portions of second dielectric layer 120, trench stop layer 115, and first dielectric layer 110, such as by using one or more etching methods now known to the art or developed in the future. The partial trenches 305 formed in the first etching step are extended deeper into the IC by the second etching step, breaking through trench stop layer 115 and extending at least partially into first dielectric layer 110. The resulting full-depth trenches 310 may be positioned between trench spacers 130.

Figure 11:
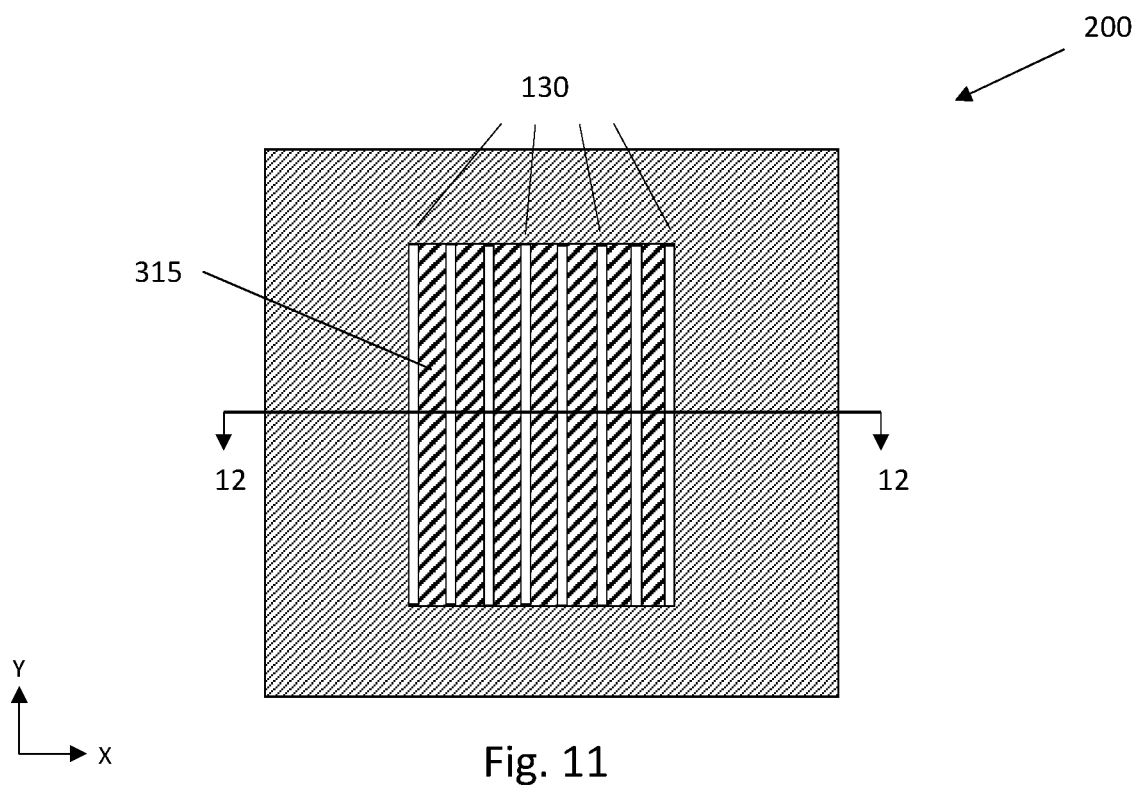
FIG. 11 shows a plan view of the IC after undergoing forming a metal in the trenches according to embodiments of this disclosure.
Figure 12:
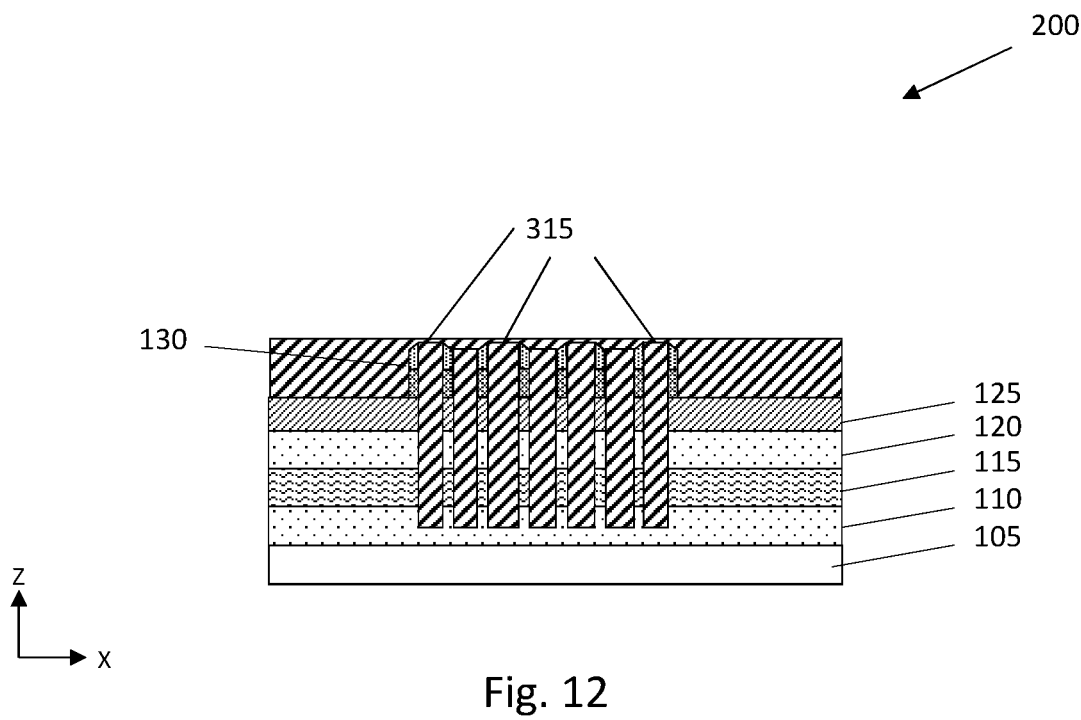
FIG. 12 shows a lateral cross section view along line 12-12 in FIG. 11 of the IC after undergoing forming of a metal according to embodiments of this disclosure.

Proceeding to FIGS. 11 and 12 together, processes for filling the previously formed marking trenches 310 according to the disclosure are shown. FIG. 11 provides a plan view of a partially processed structure 200 with metal deposited therein, while FIG. 12 provides a cross-sectional view in plane X-Z of the same structure. Processing according to embodiments of this disclosure includes depositing a metal 315 in the full-depth trenches 310. Although metal 315 is only show in full-depth trenches 310, metal may be deposited on other portions of the IC not shown for clarity. In any case, metal 315 formed in the full-depth trenches 310 according to embodiments of this disclosure may be electrically isolated from any active devices which are also present.

Metal 315 deposited in the full-depth marking trenches 310 can be in the form of any currently known or later developed conductive material such as, e.g., aluminum (Al), zinc (Zn), indium (In), copper (Cu), indium copper (InCu), tin (Sn), tantalum (Ta), tantalum nitride (TaN), tantalum carbide (TaC), titanium (Ti), titanium nitride (TiN), titanium carbide (TiC), tungsten (W), tungsten nitride (WN), tungsten carbide (WC), cobalt (Co), ruthenium (Ru), and/or polysilicon (poly-Si) or combinations thereof. In some cases, metal 315 may be deposited within full-depth trenches 310 concurrently with other metal deposition techniques to form other conductive elements of an IC structure. In such cases, metal wires, vias, etc., may be formed on laterally distal regions (not shown) of the device structure through damascene or other procedures for filling an opening in a layer with a conductive metal. As shown by example in FIG. 12, metal 315 may be formed to at least the height of any remaining trench spacers 130. The prior formation of full-depth trenches 310 may allow full-depth trenches 310 to be filled with metal 315 concurrently with other openings in an IC structure.

Figure 13:
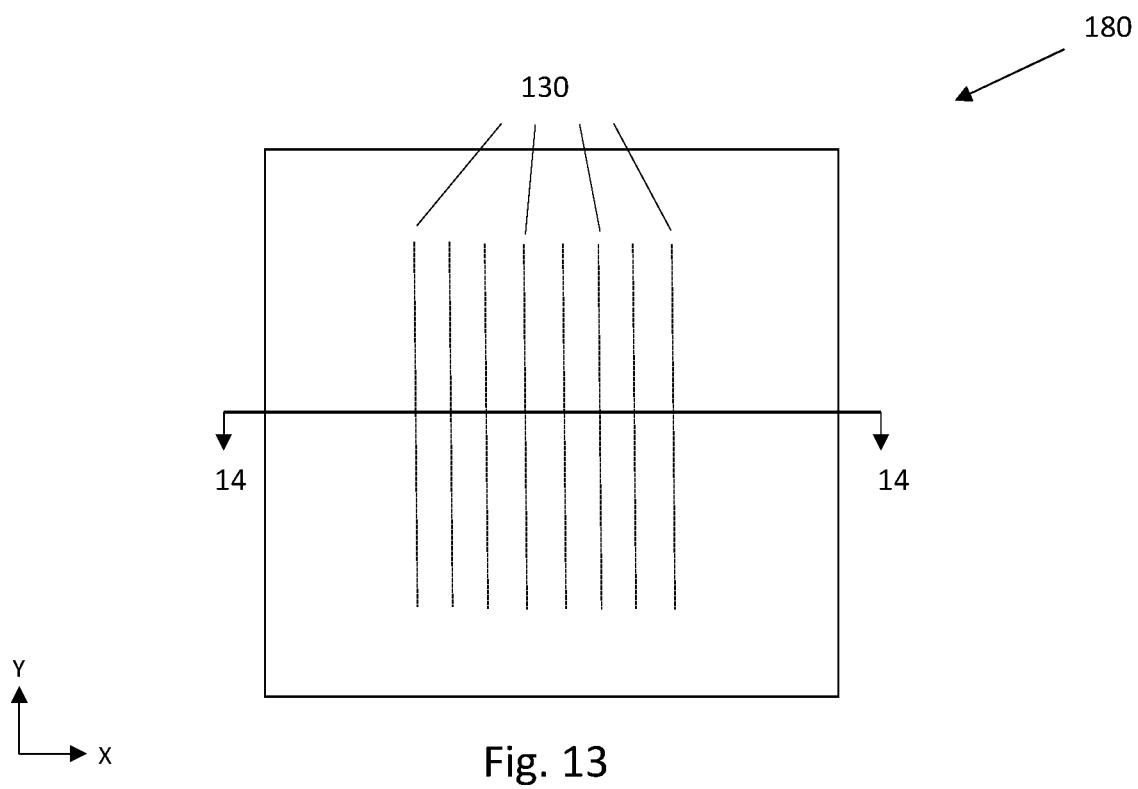
FIG. 13 shows a plan view of another precursor structure of an integrated circuit (IC) to be processed according to embodiments of this disclosure.

Referring now to FIGS. 13 and 14, the various processes implemented on precursor structure 100 (FIGS. 1, 2) and partially processed structure (FIGS. 3-12) may be implemented on a precursor structure 180 with different structural characteristics. Precursor structure 180 shown in FIGS. 13,14 may include substantially the same components as precursor structure 100 shown in FIGS. 1,2, but may have additional or alternative structural features. In particular, precursor structure 180 may be formed by way of a processes other than SADP (self-aligned double patterning). As shown in FIG. 14, forming precursor structure 180 without SADP may yield a series of preformed openings 182 extending at least partially into first hard mask 125, and without trench spacers 130 (FIGS. 1-12). As shown, an upper surface of second dielectric layer 120 may be located at the bottom of one or more openings 182. The remaining components of precursor structure 180 may be the same as those in precursor structure 100.

Although precursor structure 180 may include one or more structural differences as compared to precursor structure 100, the embodiments of the processes described herein relative to FIGS. 1-12 may be suitable to form an IC structure 300 (FIGS. 25-28, discussed below) for alignment of different layers in a device. It is therefore emphasized that the processes discussed herein and shown in the accompanying FIGS. 13-24 reflect a similar or identical set of processing concepts with possible variances in implementation, discussed herein, to be performed on alternative precursor structure 180.

Figure 15:
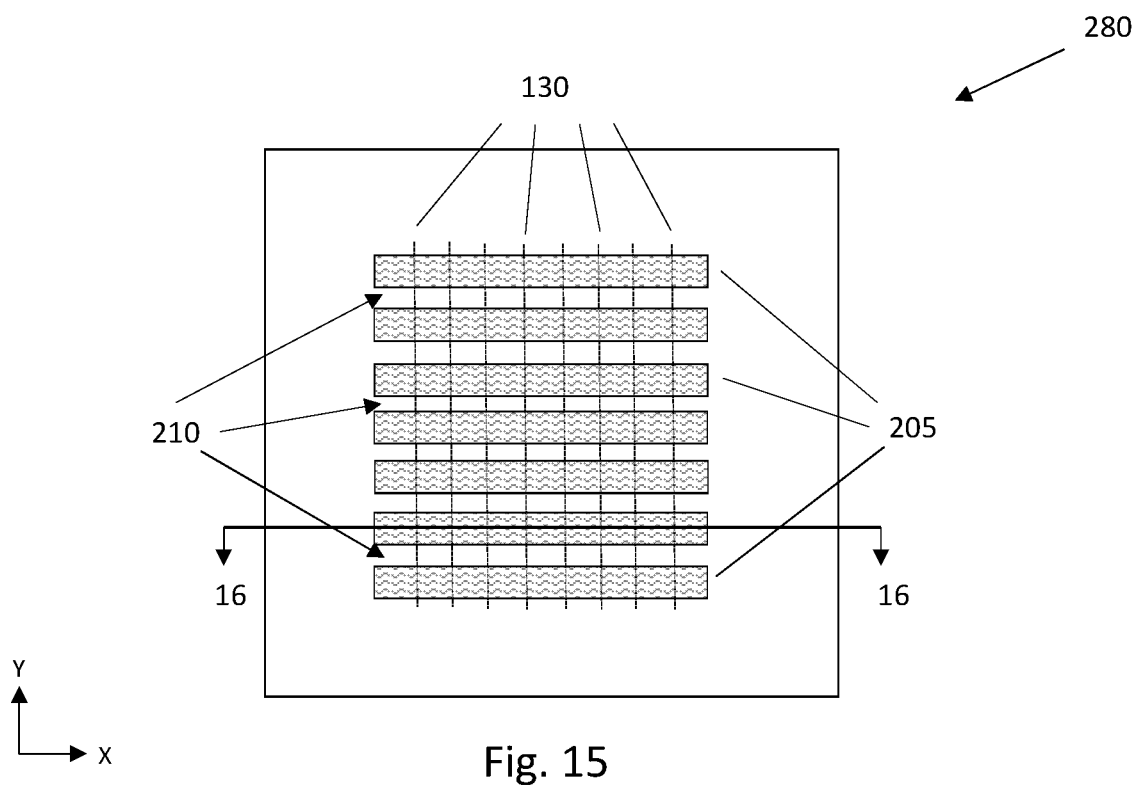
FIG. 15 shows a plan view of the IC after undergoing a first patterning operation according to embodiments of this disclosure.
Figure 16:
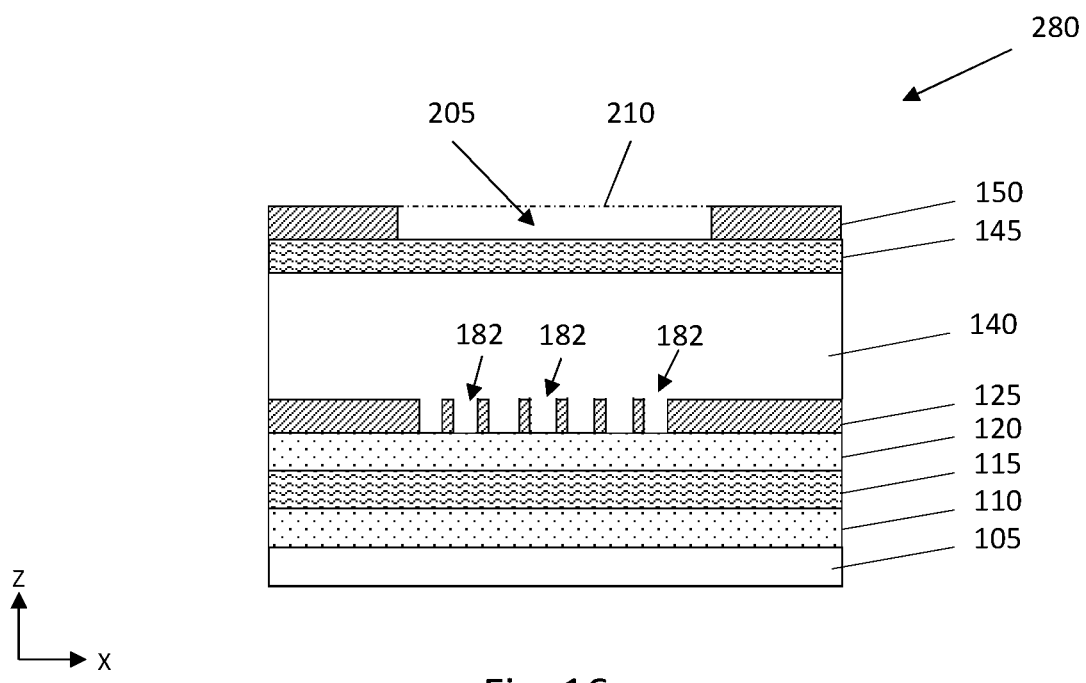
FIG. 16 shows a lateral cross section view along line 16-16 in FIG. 15 of the IC after undergoing a first patterning operation according to embodiments of this disclosure.
Figure 17:
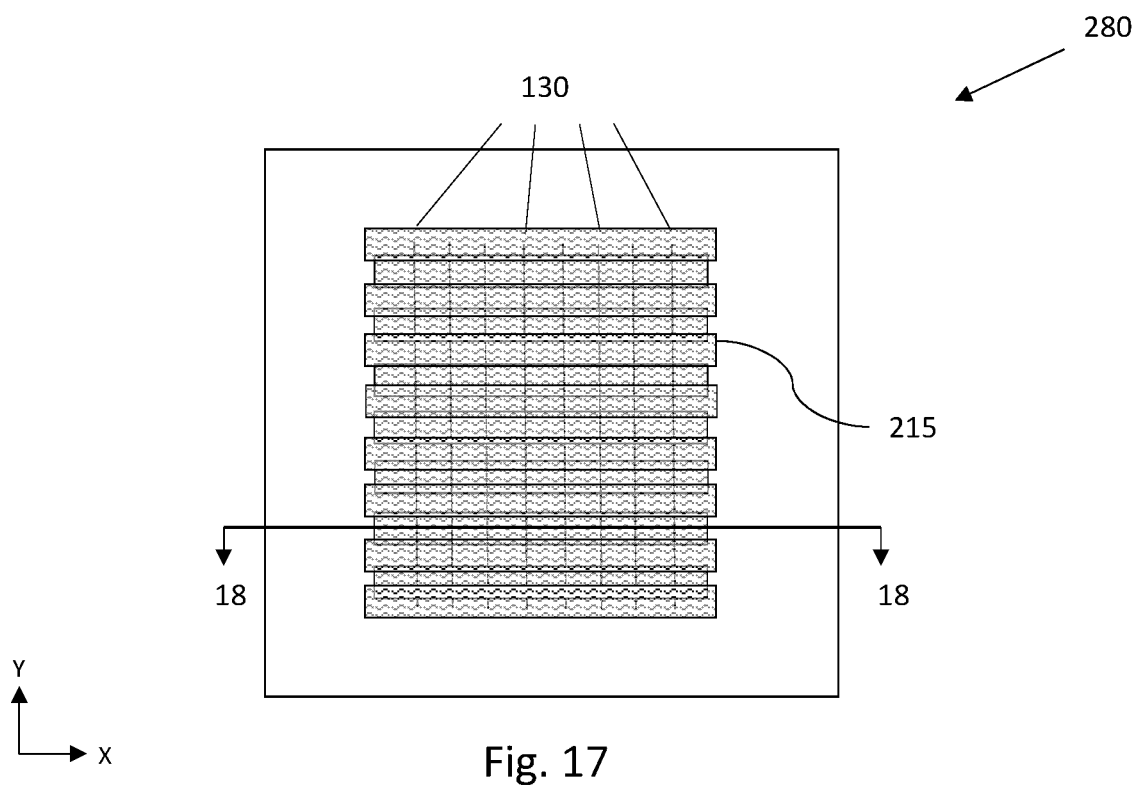
FIG. 17 shows a plan view of the IC after undergoing a second patterning operation according to embodiments of this disclosure.
Figure 18:
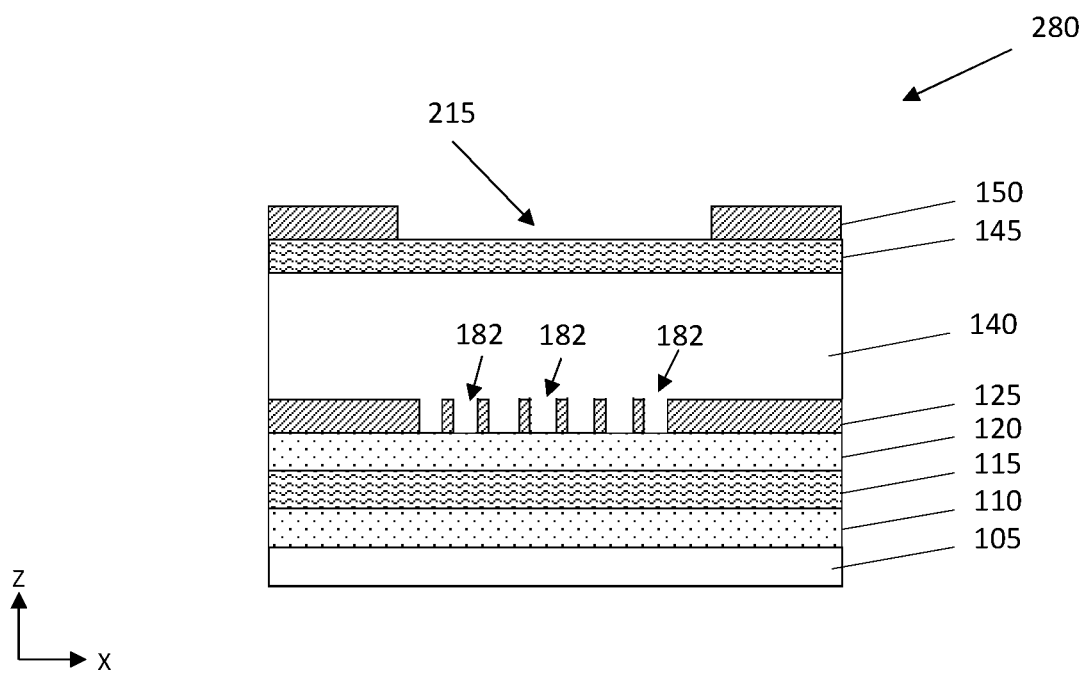
FIG. 18 shows a lateral cross section view along line 18-18 in FIG. 17 of the IC after undergoing a second patterning operation according to embodiments of this disclosure.
Figure 19:
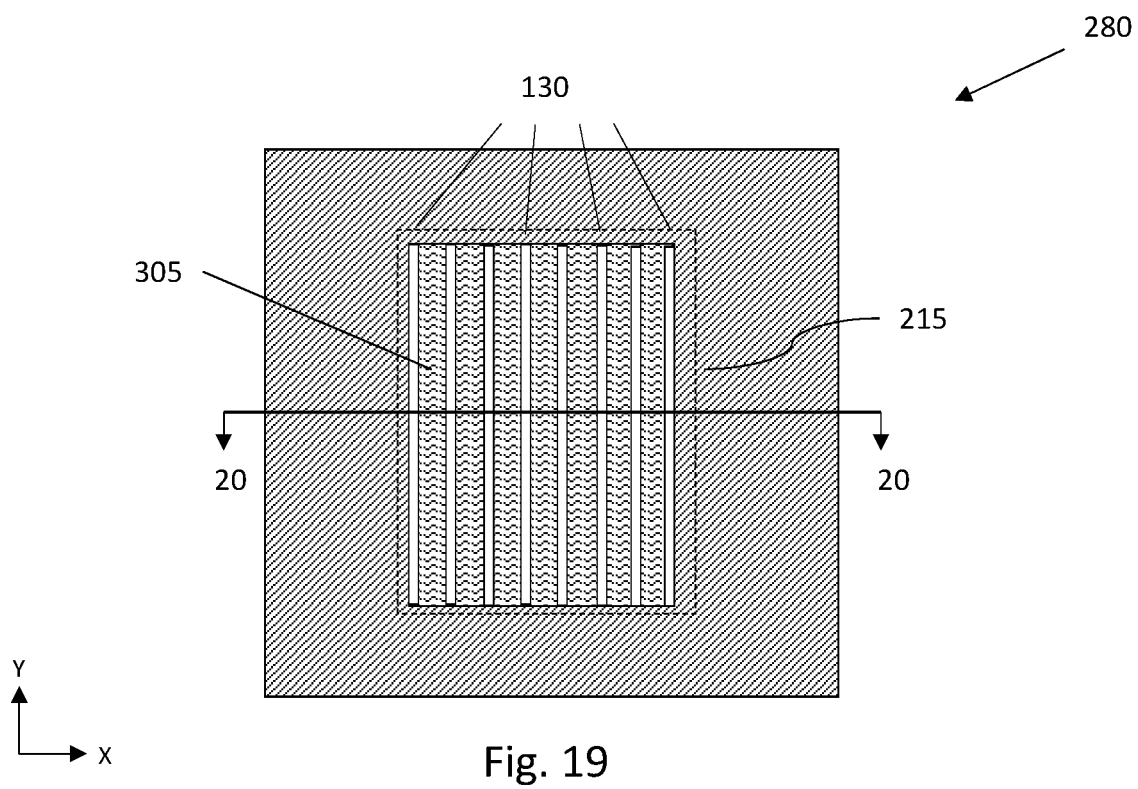
FIG. 19 shows a plan view of the IC after undergoing a first removal operation according to embodiments of this disclosure.
Figure 20:
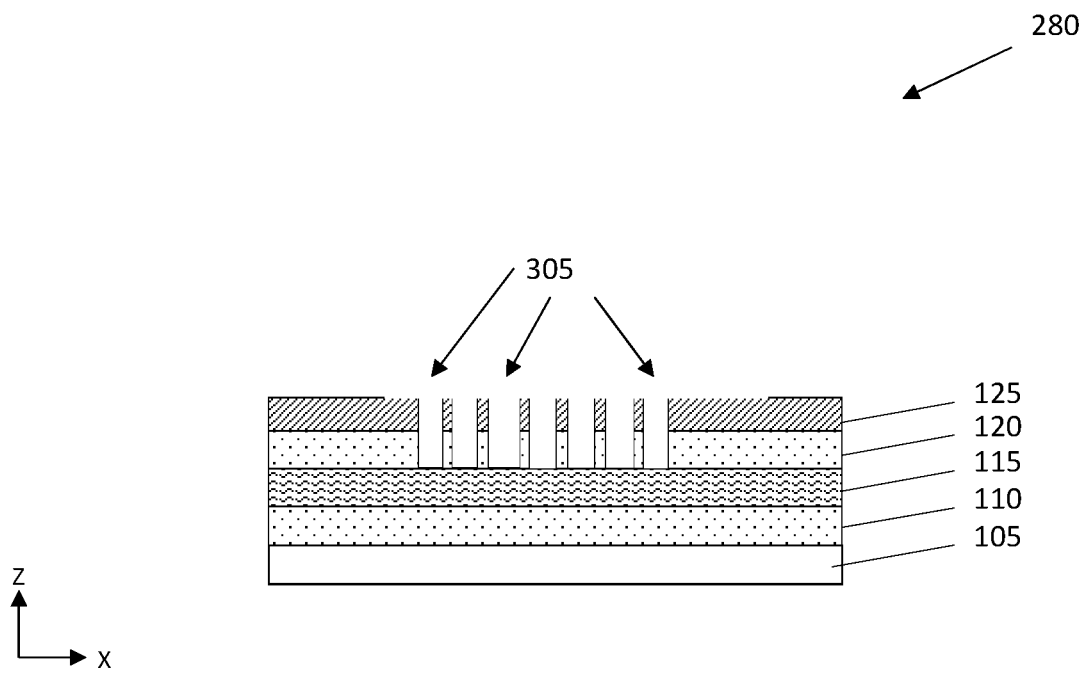
FIG. 20 shows a lateral cross section view along line 20-20 in FIG. 19 of the IC after undergoing a first removal operation according to embodiments of this disclosure.
Figure 21:
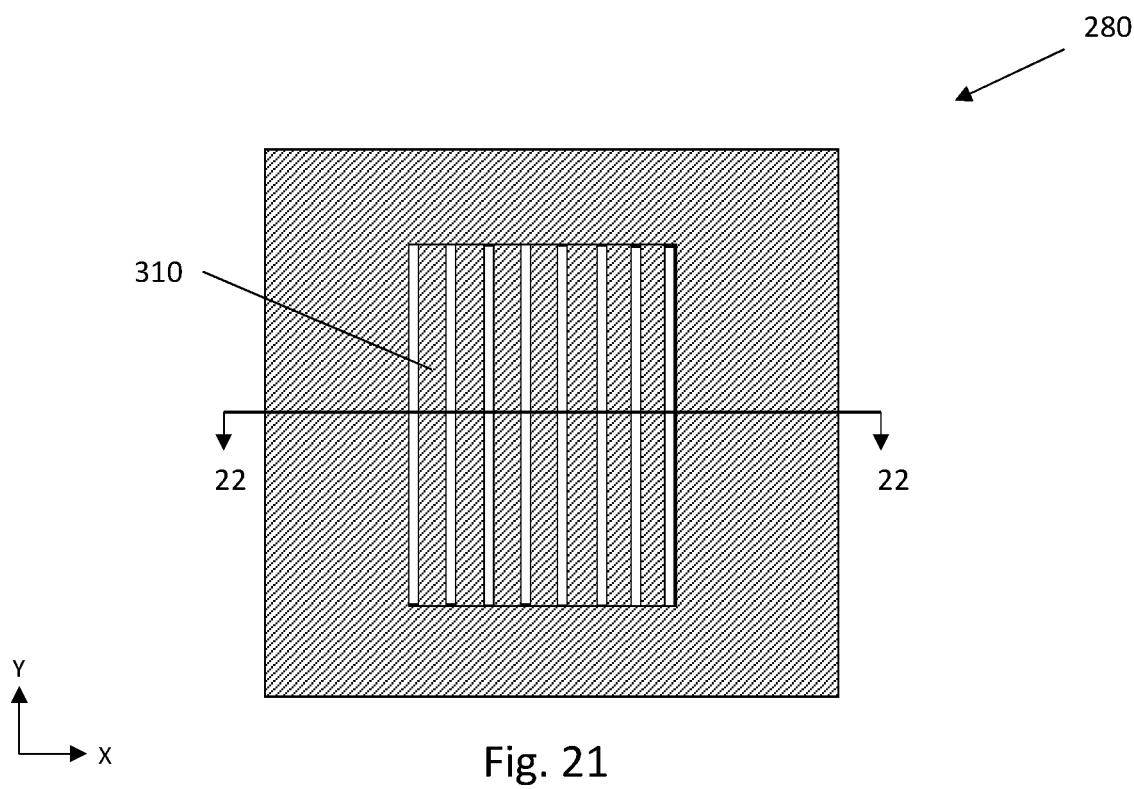
FIG. 21 shows a plan view of the IC after undergoing a second removal operation according to embodiments of this disclosure.
Figure 22:
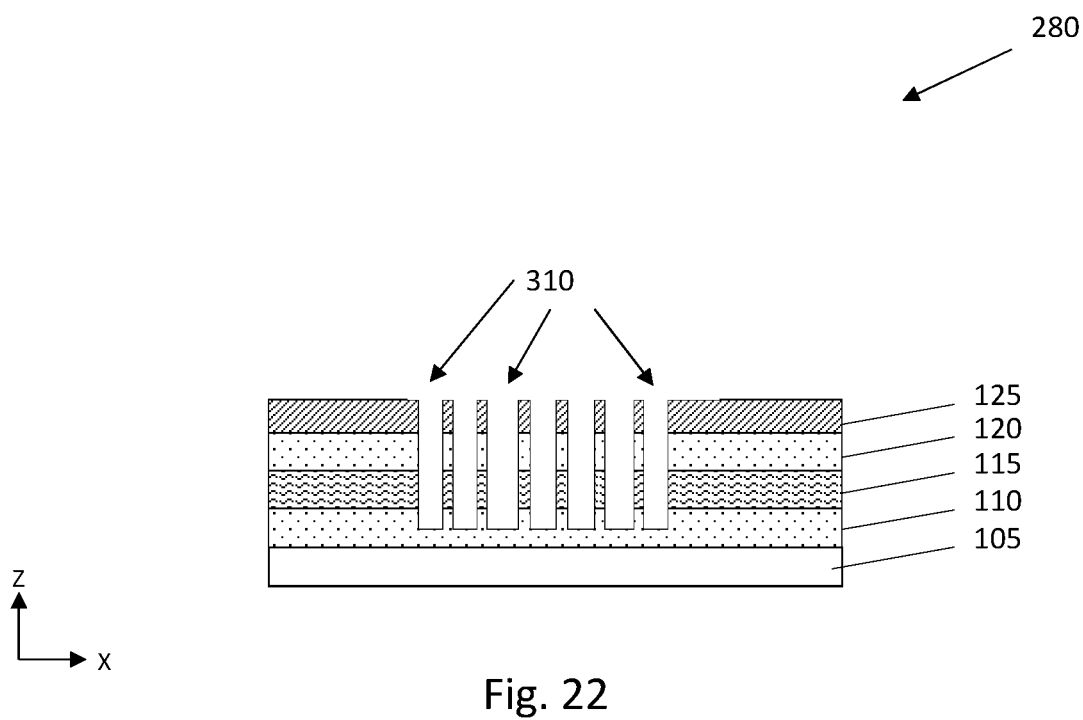
FIG. 22 shows a lateral cross section view along line 22-22 in FIG. 21 of the IC after undergoing a second removal operation according to embodiments of this disclosure.

Precursor structure 180 may be processed into partially-processed structure(s) 280 (FIGS. 15-24) using the same or similar processes discussed herein relative to precursor structure 100 (FIGS. 1, 2) and partially-processed structure(s) 200 (FIGS. 3-12). Except where noted otherwise herein, the various processing operations, materials, etc., discussed relative to FIGS. 1-12 may also be used for operations on precursor structure 180 and partially processed structure(s) 280. FIGS. 15 and 16 illustrate forming openings 205 in via hard mask 150. FIGS. 17 and 18 demonstrate forming expanded openings 215 in via hard mask 150, e.g., by using a second color mask to increase the size of the previously formed openings in hard mask 205. Applying a second lithography step may remove substantially all of via hard mask 150 preformed openings 182. Continued manufacture as shown in FIGS. 18 and 19 may include, e.g., forming marking trenches 305 by removing via hard mask 150, via stop layer 145, and spin-on hard mask 140. Portions of first hard mask 125 and second dielectric 120 may be removed beneath expanded opening 215, forming partial marking trenches 305. Referring now to FIGS. 21 and 22, processing may continue by etching partial marking trenches 305 to yield full-depth marking trenches 310 therein, but without trench spacers 130 being present on first hard mask 125. Partially-processed structure 280 then may be planarized such that first hard mask 125 has a horizontally planar upper surface.

Figure 23:
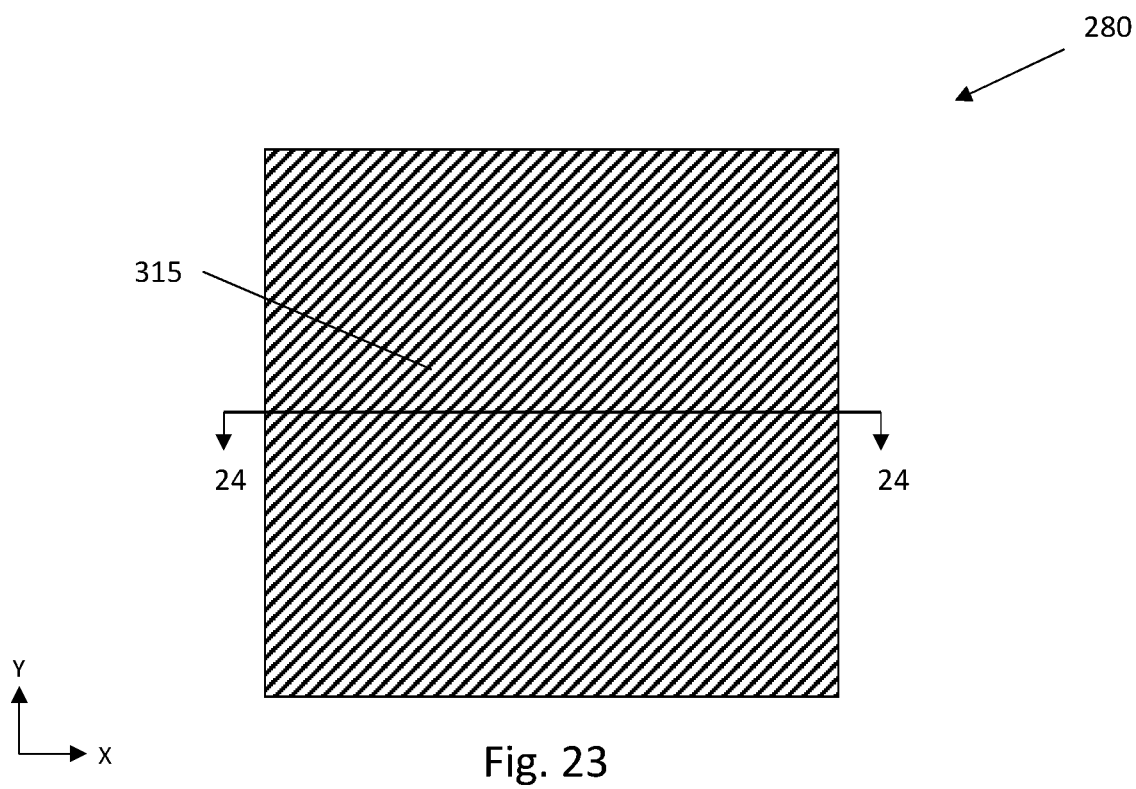
FIG. 23 shows a plan view of the IC after undergoing forming a metal in the trenches according to embodiments of this disclosure.
Figure 24:
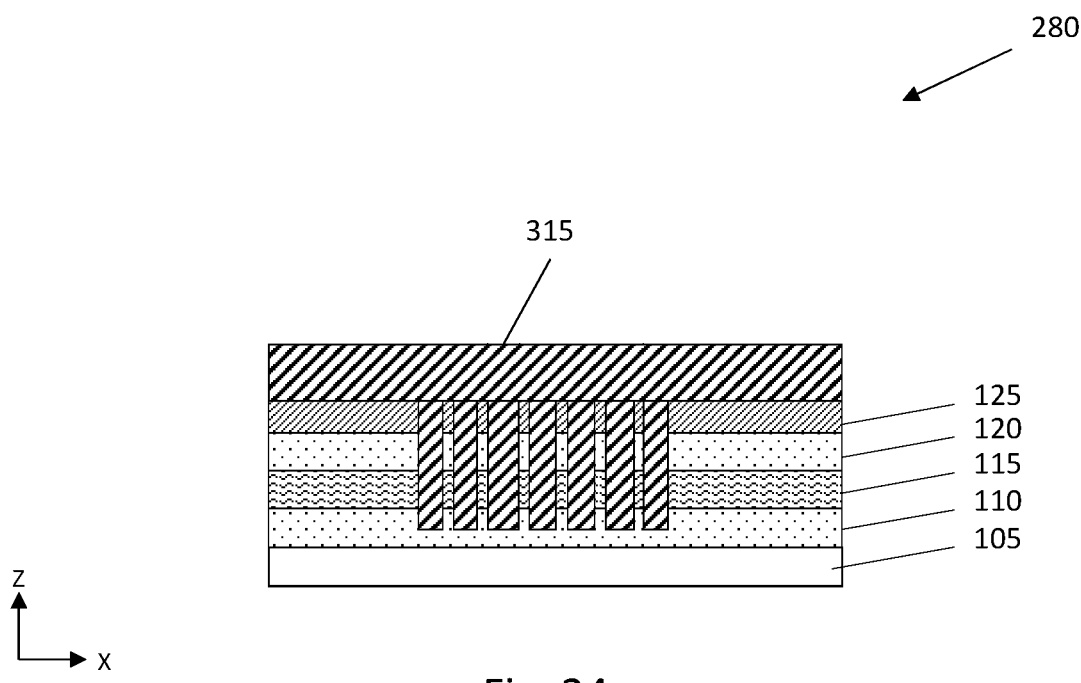
FIG. 24 shows a lateral cross section view along line 24-24 in FIG. 23 of the IC after undergoing forming a metal according to embodiments of this disclosure.

FIGS. 23 and 24 illustrate forming metal 315 on partially-processed structure 280. The processes of forming metal 315, e.g., deposition, on partially-processed structure 280 may be the same as those discussed elsewhere herein relative to forming metal 315 on partially processed structure 200, and shown in FIGS. 11 and 12. In this case, however, the absence of trench spacers 130 in partially-processed structure 280 may cause metal 315 to be formed on, and entirely cover, first hard mask 125. This may be the case in still further embodiments or precursor structures, e.g., where metal is non-selectively deposited outside full-depth marking trenches 310. As discussed in detail below, metal 315 may then be planarized to the upper surface of first hard mask 125 such that metal 315 is only positioned within full-depth marking trenches 310. In embodiments where one or more trench spacers 130 have not been previously removed, the subsequent planarizing of metal 315 may also remove any remaining trench spacers 130.

Figure 25:
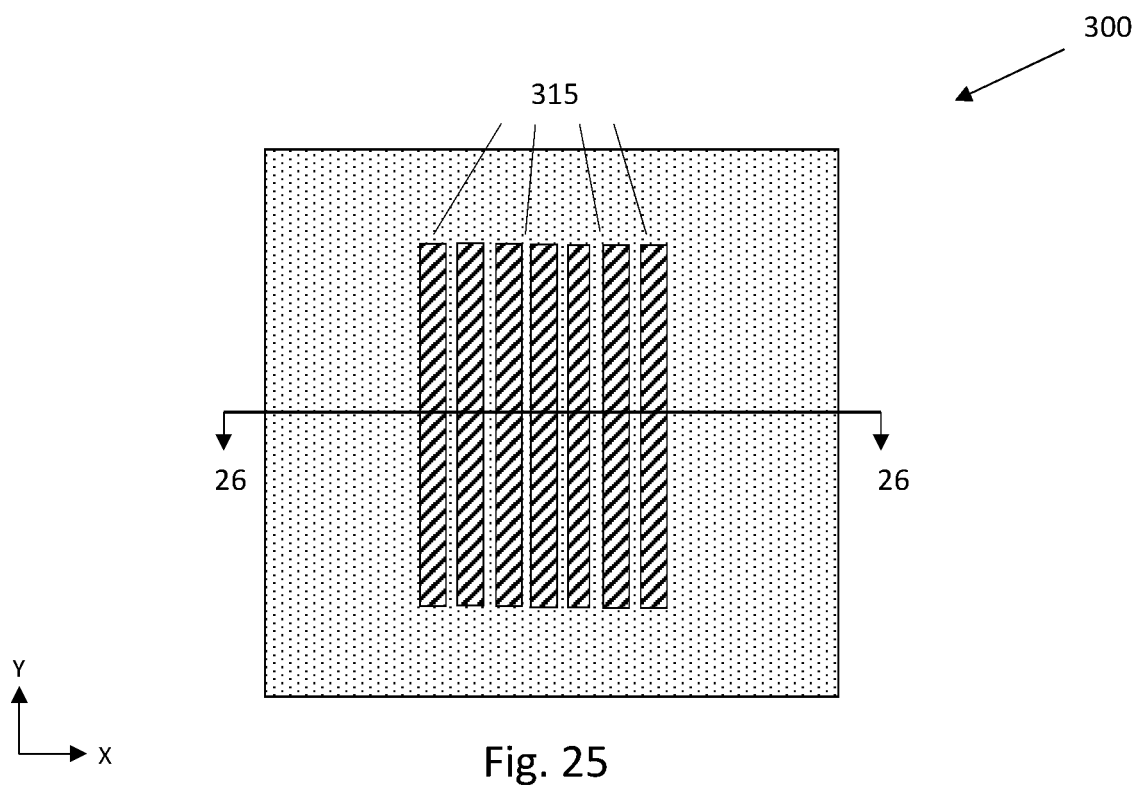
FIG. 25 shows a plan view of the IC after undergoing planarization according to embodiments of this disclosure.
Figure 26:
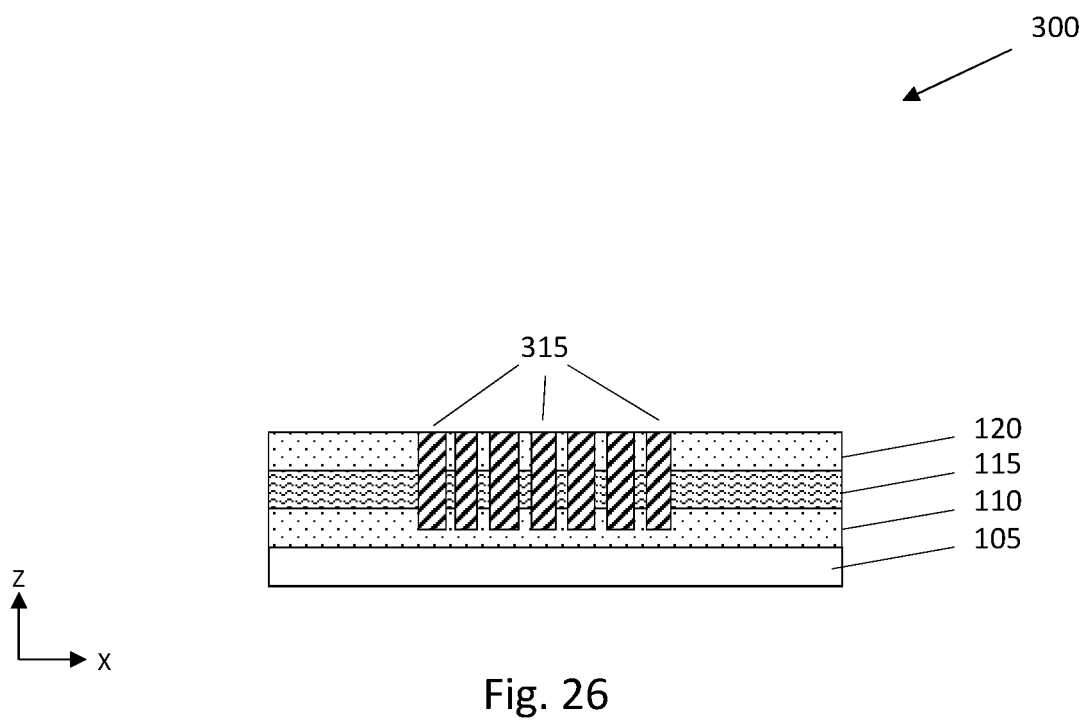
FIG. 26 shows a lateral cross section view along line 26-26 in FIG. 25 of the IC after undergoing planarization according to embodiments of this disclosure.

Proceeding to FIGS. 25 and 26 together, processes for forming finished marking trenches 315 and the corresponding IC structure 300 according to the disclosure are shown. It is noted that FIGS. 25 and 26 may represent continued processing of partially-processed structure 200 (FIGS. 3-12), partially-processed structure 280 (FIGS. 14-26), or other materials formed by the processing of other precursor structures. FIG. 25 provides a plan view of IC structure 300 with planarized metal-filled marking trenches 315 therein, while FIG. 26 provides a cross-sectional view in plane X-Z of the same structure. Processing according to this step of embodiments of this disclosure includes planarization. Planarization may remove trench spacers 130, first hard mask 125, portions of second dielectric 125, and portions of metal 315. After planarization, the upper surface of the metal will be substantially co-planar with the upper surface of second dielectric layer 120.

Planarization refers to various processes that make a surface more planar (that is, more flat and/or smooth). Chemical-mechanical-polishing (CMP) is one currently conventional planarization process which planarizes surfaces with a combination of chemical reactions and mechanical forces. CMP uses slurry including abrasive and corrosive chemical components along with a polishing pad and retaining ring, typically of a greater diameter than the wafer. The pad and wafer are pressed together by a dynamic polishing head and held in place by a plastic retaining ring. The dynamic polishing head is rotated with different axes of rotation (that is, not concentric). This process removes material and tends to even out any "topography," making the wafer flat and planar. Other currently conventional planarization techniques may include: (i) oxidation; (ii) chemical etching; (iii) taper control by ion implant damage; (iv) deposition of films of low-melting point glass; (v) resputtering of deposited films to smooth them out; (vi) photosensitive polyimide (PSPI) films; (vii) new resins; (viii) low-viscosity liquid epoxies; (ix) spin-on glass (SOG) materials; and/or (x) sacrificial etch-back.

Marking trenches 310 (as shown in FIG. 12) formed according to embodiments of this disclosure extend further into the IC structure than those formed by conventional methods. As a result, metal 315 filling the trenches will be thicker. Thicker metal provides higher contrast against the background and decreases the sensitivity to variations in metal thickness when imaging the marking trenches during subsequent processing of the IC.

Figure 27:
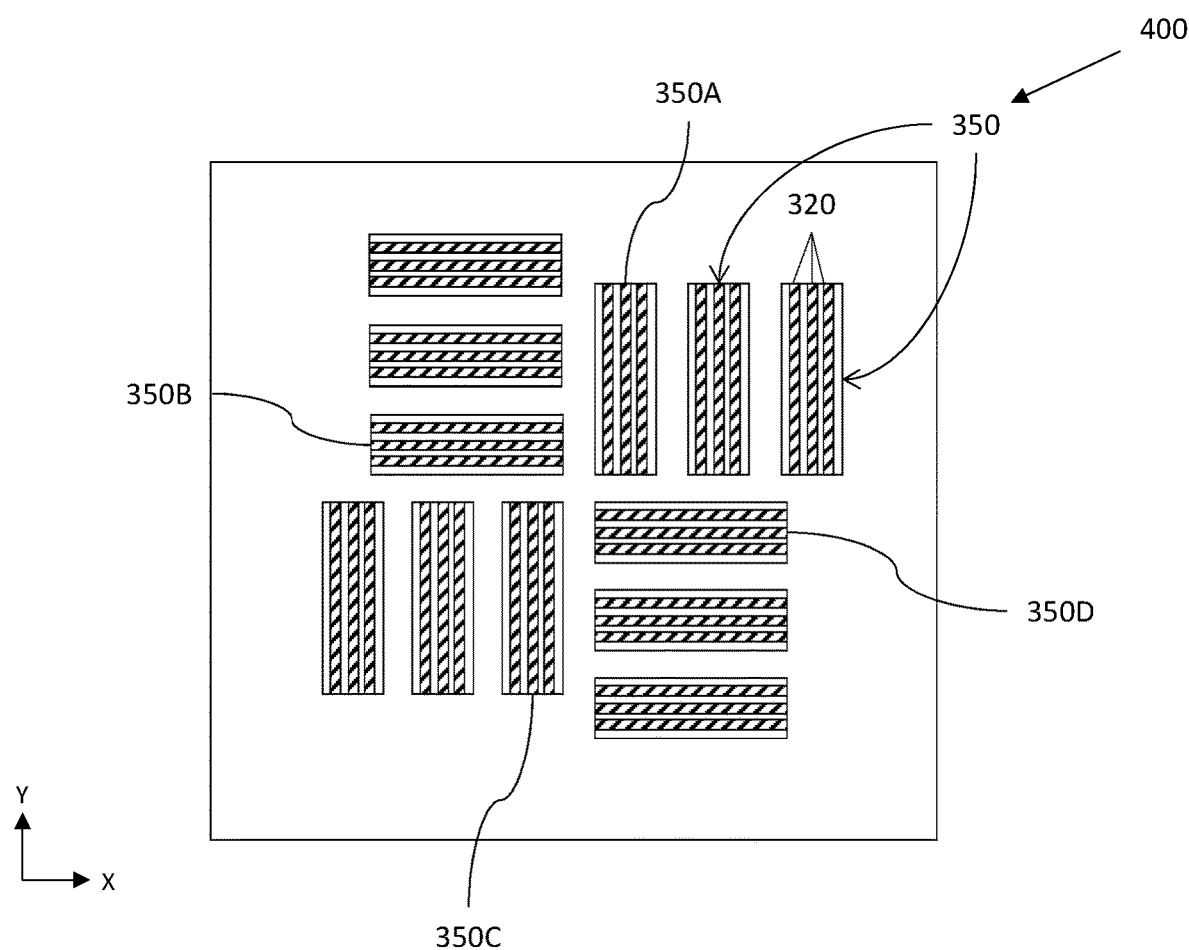
FIG. 27 shows a plan view of one embodiment of a structure according to embodiments of this disclosure.

Proceeding to FIG. 27, an example is shown of a structure 400 for that may be y fabricating a plurality of sets 350 of marking trenches 320 according to one or more of the process methods discussed above. Marking trenches 320 within each set 350 may be arranged parallel to one another and in close proximity to one another, for example with separation distances between pairs of marking trenches 320 in the range of between approximately 15 nanometers (nm) to approximately 200 nm. In some embodiments the separation distance within a set 350 is substantially the same for each pair of adjacent marking trenches 320, while in other embodiments the separation distance may vary within a set 350. Likewise, the width of marking trenches 320 may be substantially the same or may be different in different portions of set 350. Each set may be oriented in a substantially longitudinal direction (i.e., with the marking trenches extending along the Y axis), in a substantially latitudinal direction (i.e., with the marking trenches extending along the X axis), or in an oblique direction relative to the X and Y axes. In some embodiments, the spacing between sets 350 is greater than the spacing between marking trenches within each set. In other embodiments, the orientation of marking trenches within one set are different than the orientation of marking trenches within adjacent sets. In one embodiment, structure 400 for use as a metrology overlay or alignment mark includes an arrangement of at least four sets of marking trenches (350A, 350B, 350C, 350D) arranged laterally adjacent to one another such that first set 350A and third set 350C are oriented in one direction, and second set 350B and fourth set 350D are oriented in a second direction substantially perpendicular the first set 350A and third set 350C and arranged in a "pinwheel" formation as shown in FIG. 27. Additional sets 350 of marking trenches may optionally be arranged adjacent to and parallel to any of the four sets 350A, 350B, 350C, and 350D.

Figure 28:
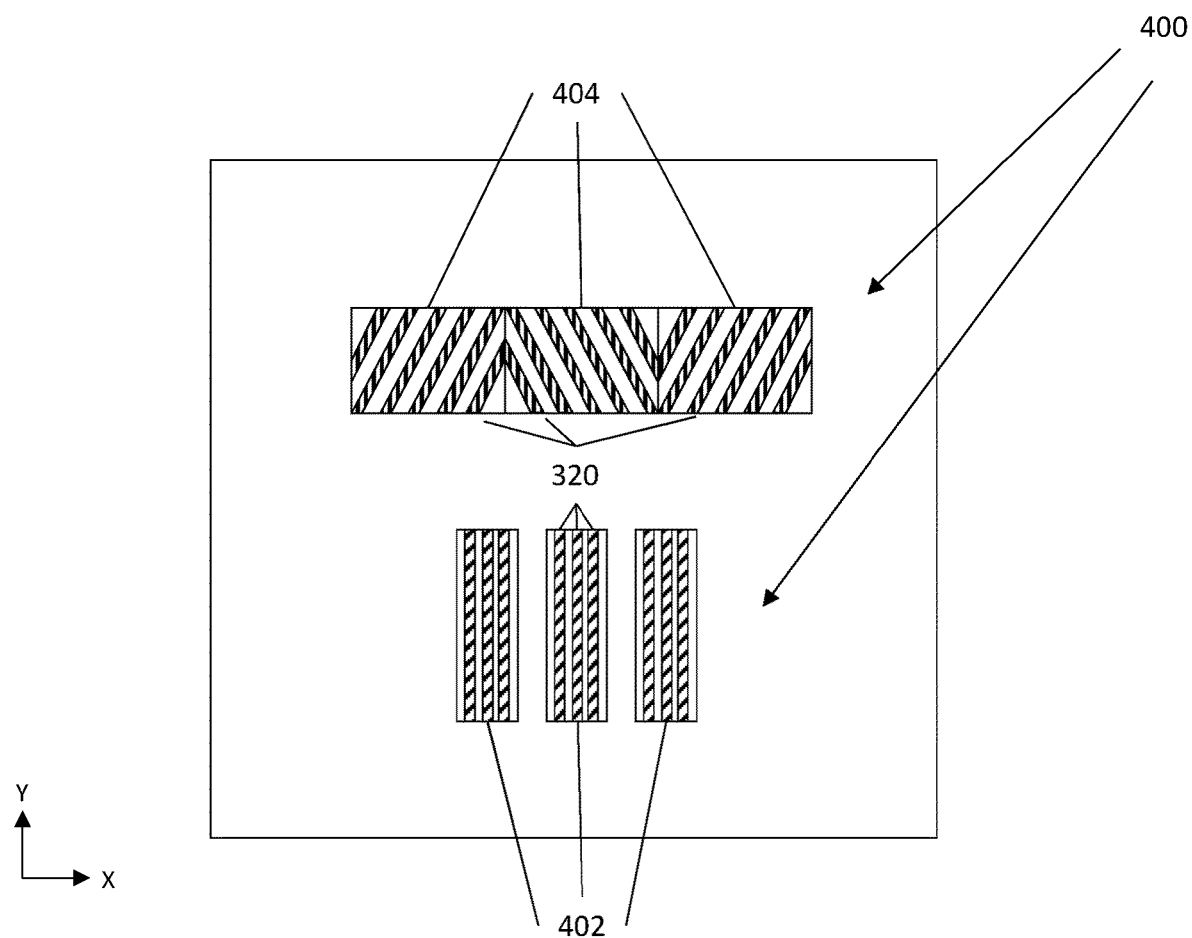
FIG. 28 shows a plan view of additional embodiments of a structure according to embodiments of this disclosure.

Referring to FIG. 28, two additional examples are shown of additional structures 400 for alignment of layers in an IC formed, e.g., fabricating a plurality of sets 350 of marking trenches 320. Many modifications and variations of the geometry of structures 400 for use as overlay or alignment marks will be apparent to those of ordinary skill in the art without departing from the scope and spirit of this disclosure. For example, without limiting the scope of this disclosure, structure 400 may include parallel sets 402 of marking trenches 320, each of which may extend laterally alongside each other along a single longitudinal axis (e.g., Y-axis as shown in FIG. 28). Parallel sets 402 of marking trenches 320 may be formed in different positions of structure 400 and may be laterally separated from each other, yet may each be shaped to occupy a substantially identical cross-sectional area of structure 400. Parallel sets of marking trenches 320 may be distinct from other arrangements discussed herein, e.g., sets 350A, 350B, 350C, 350D (FIG. 27) by extending in a single latitudinal or longitudinal direction, instead of a combination of latitudinal and/or longitudinal directions. As a further example, structure 400 may additionally or alternatively include one or more oblique sets 404 of marking trenches 320, one or more of which may have varying orientations relative to each other and/or lateral and longitudinal reference axes (e.g., axes X-Y). In the example of FIG. 28, oblique sets 404 of marking trenches 320 may have different orientations relative to adjacent oblique sets 404. According to an example, oblique sets 404 of marking trenches 320 may extend laterally diagonally in different or opposing directions, and some marking trenches 320 of each oblique set 404 may contact each other at their ends. According to still further embodiments, parallel set(s) 402 and/or oblique set(s) 404 of marking trenches 320 may be arranged to form, for example, grid-like patterns, herringbone patterns, or other arrangements suited to the particular use contemplated. The X and Y axis in various embodiments according to this disclosure may be aligned with other features of the IC or have any other orientation.

The method as described above may be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has surface interconnections and/or buried interconnections). In any case the chip is then integrated with other chips, discrete circuit elements, and/or other signal processing devices as part of either (a) an intermediate product, such as a motherboard, or (b) an end product.

The terminology used herein is for the purpose of describing particular embodiments only and is not intended to be limiting of this disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. "Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about," "approximately" and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise. "Approximately" as applied to a particular value of a range applies to both values, and unless otherwise dependent on the precision of the instrument measuring the value, may indicate +/−10% of the stated value(s). "Substantially" refers to largely, for the most part, entirely specified or any slight deviation which provides the same technical benefits of this disclosure.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to this disclosure in the form disclosed. Many modifications and variations will be apparent to those of ordinary skill in the art without departing from the scope and spirit of this disclosure. The embodiment was chosen and described in order to best explain the principles of this disclosure and the practical application, and to enable others of ordinary skill in the art to understand this disclosure for various embodiments with various modifications as are suited to the particular use contemplated.

What is claimed is:

1. A structure for aligning layers of an integrated circuit (IC), the structure comprising:
    a first dielectric layer positioned above a semiconductor substrate, the semiconductor substrate having one or more active devices thereon;
    a trench stop layer positioned above the first dielectric layer;
    a second dielectric layer positioned above the trench stop layer; and
    a plurality of metal fills each filling a respective one of a plurality of marking trenches that extend vertically through the second dielectric layer and the trench stop layer, and partially into the first dielectric layer, so that each metal fill is electrically isolated from the one or more active devices by at least the first dielectric layer,
    wherein each of the plurality of metal fills includes adjacent sidewalls substantially parallel with one another and extending vertically with respect to a top surface of the semiconductor substrate to contact each of the first dielectric layer, the trench stop layer, and the second dielectric layer, and a lowermost surface contacting the first dielectric layer and positioned above the semiconductor substrate.

2. The structure of claim 1, wherein each of the plurality of metal fills extends substantially in parallel with one another.

3. The structure of claim 2, wherein a lateral separation distance between adjacent metal fills of the plurality of metal fills is in the range of approximately 15 nanometers (nm) to approximately 200 nm.

4. The structure of claim 2, wherein the plurality of marking trenches are arranged to include:
   a first set of marking trenches having a longitudinal orientation;
   a second set of marking trenches having a latitudinal orientation substantially perpendicular to the longitudinal orientation and positioned laterally adjacent to a longitudinal end of the first set of marking trenches;
   a third set of marking trenches having the longitudinal orientation and positioned laterally adjacent to a latitudinal end of the second set of marking trenches; and
   a fourth set of marking trenches having the latitudinal orientation and positioned laterally adjacent to a longitudinal end of the third set of marking trenches and a latitudinal end of the first set of marking trenches,
   wherein the marking trenches in each set of marking trenches extends substantially in parallel with one another.

5. The structure of claim 4, wherein each set of marking trenches includes at least three marking trenches having a common orientation, and wherein a horizontal separation distance between sidewalls of adjacent sets of marking trenches is greater than an end-to-sidewall separation distance between marking trenches within each set of marking trenches.

6. The structure of claim 1, wherein the plurality of marking trenches are arranged to include:
   a first set of marking trenches; and
   a second set of marking trenches,
   wherein each of the marking trenches within the first set of marking trenches extends substantially in parallel with one another and each of the marking trenches within the second set of marking trenches extends substantially in parallel with one another.

7. The structure of claim 6, wherein each set of marking trenches includes at least three marking trenches having a common orientation, and wherein the spacing between adjacent sets of marking trenches is greater than the spacing between marking trenches within each set of marking trenches.

8. The structure of claim 6, wherein each set of marking trenches includes at least three marking trenches having a common orientation, and wherein the orientation of marking trenches is different between adjacent sets of marking trenches.

9. The structure of claim 6, wherein a lateral separation distance between adjacent metal fills is in the range of approximately 15 nanometers (nm) to approximately 200 nm.

10. The structure of claim 1, wherein the first dielectric layer is composed of a material having a dielectric constant less than 3.0.

11. The structure of claim 1, wherein the second dielectric layer comprises silicon oxide having a carbon content between 0 and 30 atomic percent.

12. The structure of claim 1, wherein at least one of the plurality of metal fills extends at least 5 nanometers (nm) beneath an upper surface of the first dielectric layer.

13. A structure for aligning layers of an integrated circuit (IC), the structure comprising:
   a first dielectric layer positioned above a semiconductor substrate, the semiconductor substrate having one or more active devices thereon;
   a trench stop layer positioned above the first dielectric layer;
   a second dielectric layer positioned above the trench stop layer;
   a first hard mask positioned above the second dielectric layer;
   a plurality of metal fills each filling a respective one of a plurality of marking trenches that extend vertically through the first hard mask, the second dielectric layer, and trench stop layer, and partially into the first dielectric layer, so that each metal fill is electrically isolated from the one or more active devices by at least the first dielectric layer; and
   a plurality of substantially parallel trench spacers positioned above the first hard mask between the plurality of marking trenches,
   wherein each metal fill within the plurality of marking trenches includes adjacent sidewalls substantially parallel with one another and extending vertically with respect to a top surface of the semiconductor substrate to contact each of the first dielectric layer, the trench stop layer, the second dielectric layer, and the first hard mask, and a lowermost surface contacting the first dielectric layer and positioned above the semiconductor substrate.

14. The structure of claim 13, wherein each of the plurality of metal fills extends substantially in parallel with one another.

15. The structure of claim 13, wherein a lateral separation distance between adjacent metal fills of the plurality of metal fills is in the range of approximately 15 nanometers (nm) to approximately 200 nm.

16. The structure of claim 13, wherein the first dielectric layer is composed of a material having a dielectric constant less than 3.0.

17. The structure of claim 13, wherein the second dielectric layer comprises silicon oxide having a carbon content between 0 and 30 atomic percent.

18. The structure of claim 13, wherein at least one of the plurality of metal fills extends at least 5 nanometers (nm) beneath an upper surface of the first dielectric layer.

19. The structure of claim 13, wherein at least one of the plurality of metal fills is filled to at least a height of the plurality of trench spacers.

* * * * *